(12) United States Patent
Hirohara et al.

(10) Patent No.: US 7,249,851 B2
(45) Date of Patent: Jul. 31, 2007

(54) EYE CHARACTERISTIC MEASURING APPARATUS

(75) Inventors: Yoko Hirohara, Tokyo (JP); Takuya Moriyama, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 578 days.

(21) Appl. No.: 10/498,229

(22) PCT Filed: Dec. 10, 2002

(86) PCT No.: PCT/JP02/12941

§ 371 (c)(1),
(2), (4) Date: Jul. 8, 2004

(87) PCT Pub. No.: WO03/053230

PCT Pub. Date: Jul. 3, 2003

(65) Prior Publication Data

US 2005/0046793 A1 Mar. 3, 2005

(30) Foreign Application Priority Data

Dec. 11, 2001 (JP) ............................ 2001-376717
Dec. 21, 2001 (JP) ............................ 2001-388965

(51) Int. Cl.
*A61B 3/10* (2006.01)
(52) U.S. Cl. .................. 351/212; 351/211; 351/239; 351/243; 351/247
(58) Field of Classification Search ............... 351/211, 351/212, 239, 243, 247
See application file for complete search history.

(56) References Cited

U.S. PATENT DOCUMENTS 6,234,978 B1  5/2001  Mihashi et al.
6,460,997 B1  10/2002 Frey et al.

(Continued)

FOREIGN PATENT DOCUMENTS

JP              8-266469 A      10/1996

(Continued)

OTHER PUBLICATIONS

N. Lopez-Gil et al., "Generation of Third-Order Spherical and Coma Aberrations by Use of Radially Symmetrical Fourth-Order Lenses", Optical Society of America, vol. 15, No. 9, Sep. 1988, pp. 2563-2571.

*Primary Examiner*—Evelyn A. Lester
(74) *Attorney, Agent, or Firm*—Foley & Lardner LLP

(57) ABSTRACT

An eye characteristic measuring apparatus can effectively and properly measure and display wavefront aberration of an eye regardless of the eye state. A first illumination optical system (200A) illuminates a small area on a retina of the eye by a first light flux from a first light source unit (100). A first reception light optical system (300A) leads a part of light flux reflected from the retina (61) to a first light reception unit (510) via a first conversion member (400) for converting the reflected light flux into at least 17 beams. A measurement data judgment unit, for example, judges whether the measurement data is appropriate for calculating the wavefront aberration according to a first signal from the first light reception unit (510). For example, when the measurement data judgment unit judges that the measurement data is not appropriate, a first correction unit causes to display a check correction screen which will be detailed later and corrects the data into appropriate measurement data. Furthermore, according to the measurement data judged to be appropriate or the measurement data which has been corrected by the first correction unit (603), a calculation unit calculates the wavefront aberration of the eye (60) as optical characteristic. Moreover, a measurement result judgement unit for example, judges whether the wavefront aberration calculated by the calculation unit is appropriate. Moreover, for example, when the measurement result judgment unit judges that the measurement result is not appropriate, a second correction unit (607) causes to display the check correction screen and correct the data into appropriate measurement data.

20 Claims, 21 Drawing Sheets

U.S. PATENT DOCUMENTS

| | | |
|---|---|---|
| 6,530,917 B1 | 3/2003 | Seiler et al. |
| 6,634,750 B2 * | 10/2003 | Neal et al. .................. 351/211 |
| 6,997,555 B2 * | 2/2006 | Dick et al. .................. 351/211 |
| 2002/0041359 A1 | 4/2002 | Mihashi et al. |
| 2003/0038921 A1 * | 2/2003 | Neal et al. .................. 351/212 |
| 2003/0058404 A1 * | 3/2003 | Thorn et al. ................ 351/212 |
| 2003/0063257 A1 * | 4/2003 | Molebny .................... 351/212 |
| 2003/0071967 A1 * | 4/2003 | Campin et al. ............. 351/211 |
| 2004/0004696 A1 * | 1/2004 | Davis et al. ................ 351/212 |
| 2005/0088618 A1 * | 4/2005 | Otten et al. ................ 351/212 |
| 2005/0094100 A1 * | 5/2005 | Ross et al. .................. 351/212 |

FOREIGN PATENT DOCUMENTS

| | | |
|---|---|---|
| JP | 10-305013 A | 11/1998 |
| JP | 2001-204690 A | 7/2001 |
| JP | 2001-321340 A | 11/2001 |
| JP | 2002-314372 A | 11/2001 |
| WO | WO 00/45759 A1 | 8/2000 |

* cited by examiner

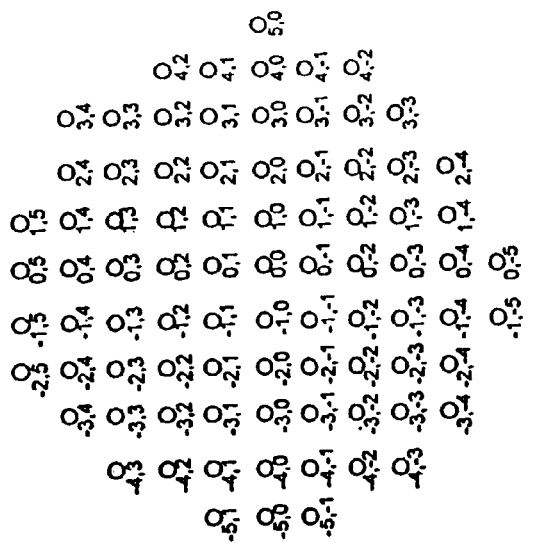
FIG. 5(c)
○ point
◯ net
⊙ number
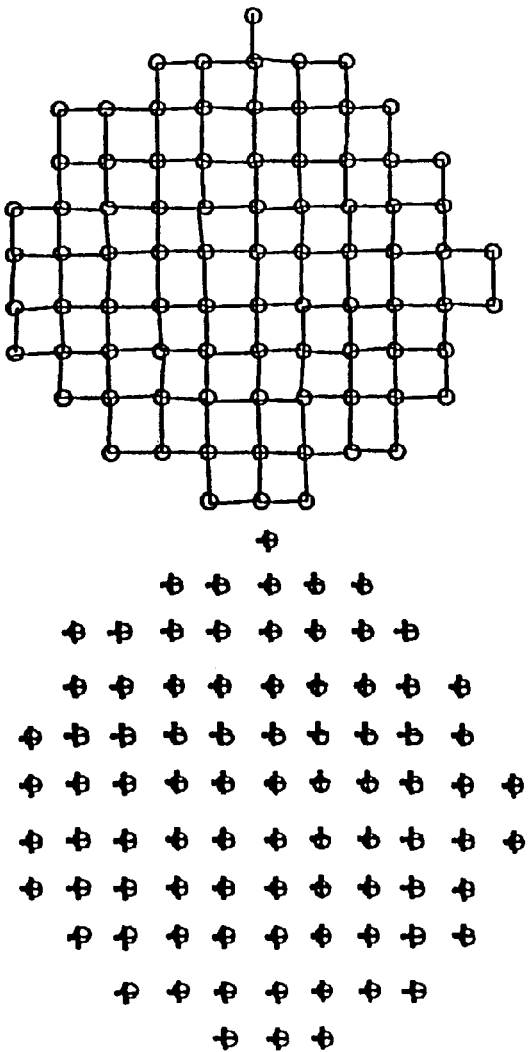
FIG. 5(b)
○ point
⊙ net
◯ number
FIG. 5(a)
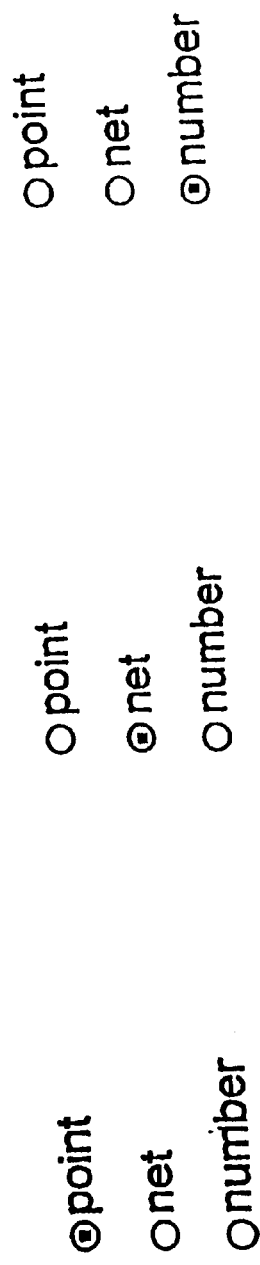
⊙ point
○ net
◯ number

DETECTION OF
CENTER OF
GRAVITY OF SPOT

FIG. 15(b)

EXAMPLE OF VERTICAL DIRECTION
ROW NUMBER DETERMINATION

FIG. 15(a)

EXAMPLE OF HORIZONTAL DIRECTION
COLUMN NUMBER DETERMINATION $$\begin{bmatrix}
i & 2j-i & \\
0 & 0 & 1 \\
1 & -1 & r\sin(t) \\
1 & 1 & \cos(t)\,r \\
2 & -2 & r^2\sin(2t) \\
2 & 0 & 2r^2-1 \\
2 & 2 & r^2\cos(2t) \\
3 & -3 & r^3\sin(3t) \\
3 & -1 & (3r^3-2r)\sin(t) \\
3 & 1 & (3r^3-2r)\cos(t) \\
3 & 3 & r^3\cos(3t) \\
4 & -4 & r^4\sin(4t) \\
4 & -2 & (4r^4-3r^2)\sin(2t) \\
4 & 0 & 6r^4-6r^2+1 \\
4 & 2 & (4r^4-3r^2)\cos(2t) \\
4 & 4 & r^4\cos(4t) \\
5 & -5 & r^5\sin(5t) \\
5 & -3 & (5r^5-4r^3)\sin(3t) \\
5 & -1 & (10r^5-12r^3+3r)\sin(t) \\
5 & 1 & (10r^5-12r^3+3r)\cos(t) \\
5 & 3 & (5r^5-4r^3)\cos(3t) \\
5 & 5 & r^5\cos(5t) \\
6 & -6 & r^6\sin(6t) \\
6 & -4 & (6r^6-5r^4)\sin(4t) \\
6 & -2 & (15r^6-20r^4+6r^2)\sin(2t) \\
6 & 0 & 20r^6-30r^4+12r^2-1 \\
6 & 2 & (15r^6-20r^4+6r^2)\cos(2t) \\
6 & 4 & (6r^6-5r^4)\cos(4t) \\
6 & 6 & r^6\cos(6t)
\end{bmatrix}$$

FIG. 20

$$\begin{bmatrix}
i & 2j-i & \\
0 & 0 & 1 \\
1 & -1 & y \\
1 & 1 & x \\
2 & -2 & 2yx \\
2 & 0 & 2x^2 + 2y^2 - 1 \\
2 & 2 & x^2 - y^2 \\
3 & -3 & 3yx^2 - y^3 \\
3 & -1 & 3yx^2 + 3y^3 - 2y \\
3 & 1 & 3x^3 + 3xy^2 - 2x \\
3 & 3 & x^3 - 3xy^2 \\
4 & -4 & 4yx^3 - 4y^3 x \\
4 & -2 & 8yx^3 + 8y^3 x - 6yx \\
4 & 0 & 6x^4 + 12x^2 y^2 + 6y^4 - 6x^2 - 6y^2 + 1 \\
4 & 2 & 4x^4 - 4y^4 - 3x^2 + 3y^2 \\
4 & 4 & x^4 - 6x^2 y^2 + y^4 \\
5 & -5 & 5yx^4 - 10y^3 x^2 + y^5 \\
5 & -3 & 15yx^4 + 10y^3 x^2 - 5y^5 - 12yx^2 + 4y^3 \\
5 & -1 & 10yx^4 + 20y^3 x^2 + 10y^5 - 12yx^2 - 12y^3 + 3y \\
5 & 1 & 10x^5 + 20x^3 y^2 + 10xy^4 - 12x^3 - 12xy^2 + 3x \\
5 & 3 & 5x^5 - 10x^3 y^2 - 15xy^4 - 4x^3 + 12xy^2 \\
5 & 5 & x^5 - 10x^3 y^2 + 5xy^4 \\
6 & -6 & 6yx^5 - 20y^3 x^3 + 6y^5 x \\
6 & -4 & 24yx^5 - 24y^5 x - 20yx^3 + 20y^3 x \\
6 & -2 & 30yx^5 + 60y^3 x^3 + 30y^5 x - 40yx^3 - 40y^3 x + 12yx \\
6 & 0 & 20x^6 + 60x^4 y^2 + 60x^2 y^4 + 20y^6 - 30x^4 - 60x^2 y^2 - 30y^4 + 12x^2 + 12y^2 - 1 \\
6 & 2 & 15x^6 + 15x^4 y^2 - 15x^2 y^4 - 15y^6 - 20x^4 + 20y^4 + 6x^2 - 6y^2 \\
6 & 4 & 6x^6 - 30x^4 y^2 - 30x^2 y^4 + 6y^6 - 5x^4 + 30x^2 y^2 - 5y^4 \\
6 & 6 & x^6 - 15x^4 y^2 + 15x^2 y^4 - y^6
\end{bmatrix}$$

FIG. 21

EYE CHARACTERISTIC MEASURING APPARATUS

TECHNICAL FIELD

The present invention relates to an eye characteristic measuring apparatus, and particularly to an eye characteristic measuring apparatus which can more efficiently and properly measure and display the wavefront aberration of a subject eye.

BACKGROUND OF THE INVENTION

As a conventional corneal shape measuring apparatus, there is known an apparatus in which an index is projected and an imaging position of the index is obtained to measure a corneal shape. Besides, as an apparatus for measuring optical characteristics of an eye, especially as one disclosed in a patent application filed by the present applicant, there is an apparatus in which the pint adjustment of an illumination optical system is performed by use of the light reception level of a first light reception unit, and the pint adjustment of a light reception optical system is performed on the basis of the optical characteristic (S) obtained from the output of the first light reception unit (patent application claiming domestic priority based on Japanese Patent Application No. 9-137630, Japanese Patent Application No. 10-146562 (JP-A-11-028188))

SUMMARY OF THE INVENTION

However, in the conventional eye characteristic measuring apparatus, it is supposed that a disadvantage occurs in a case of measurement of a diseased eye such as a keratoconus. For example, with respect to the extraction of spot images from a Hartmann image based on faint reflected light from an retina, it is supposed to be difficult to automatically extract them in a case where an aberration of a subject eye is large, or in a case where transmittance in an eye is low or scattering is high.

Especially, in the case where the subject eye is not normal, it is supposed to be difficult to extract such spot images. Up to now, it has been desired to perform a correcting operation in an efficient procedure and to make a wavefront measurement even in the case as stated above.

Besides, in general, in the case where a shift from a reference lattice point occurs, there is a tendency that with respect to spot images of a Hartmann image, lattice intervals in the horizontal direction are substantially constant, and unevenness occurs in the lattice intervals in the vertical direction. Then, as a direction in which lattice points are determined so that measurements of eyes of many people can be automatically and certainly measured, it is supposed that priority is given to the horizontal direction. However, with respect to an eye with astigmatism against the rule, abnormal cornea, failure in a cornea operation or the like, for example, the lattice intervals in the horizontal direction can be uneven. It has been desired up to now that even in the foregoing case, an accurate wavefront measurement is performed.

In view of the above, one of objects of the invention is to provide an eye characteristic measuring apparatus which can more efficiently and properly measure and display the wavefront aberration of a subject eye irrespective of the state of the subject eye. Besides, another object of the invention is to provide an eye characteristic measuring apparatus in which before measurement of wavefront aberration and/or after the measurement, a correcting operation is performed in an efficient procedure and the measurement of the wavefront aberration can be again performed.

Besides, another object of the invention is to provide an eye characteristic measuring apparatus in which spot images of a Hartmann image are made to correspond to lattice points and an illumination state can be made appropriate.

According to first solving means of the invention, an eye characteristic measuring apparatus includes a light source unit for emitting a light flux with a first wavelength, a first illumination optical system for illuminating a small area on a retina of a subject eye with the light flux from the light source unit, a first light reception optical system for leading a part of a first reflected light flux reflected by and returning from the retina of the subject eye to be received through a first conversion member for converting it into at least substantially 17 beams, a first light reception unit for receiving the received light flux of the first light reception optical system to form a first signal, a measurement data judgment unit for judging, on the basis of the first signal from the first light reception unit, whether measurement data is appropriate for obtaining a wavefront aberration, a first correction unit for causing a check correction screen to be displayed when the measurement data judgment unit judges that the measurement data is inappropriate and for correcting it into appropriate measurement data, a calculation unit for calculating the wavefront aberration of the subject eye as optical characteristic on the basis of the measurement data which has been judged to be appropriate by the measurement data judgment unit or the measurement data which has been corrected by the first correction unit, and a display unit for displaying the wavefront aberration as a calculation result of the calculation unit.

According to second solving means of the invention, an eye characteristic measuring apparatus includes a light source unit for emitting a light flux with a first wavelength, a first illumination optical system for illuminating a small area on a retina of a subject eye with the light flux from the light source unit, a first light reception optical system for leading a part of a first reflected light flux reflected by and returning from the retina of the subject eye to be received through a first conversion member for converting it into at least substantially 17 beams, a first light reception unit for receiving the received light flux of the first light reception optical system to form a first signal, a calculation unit for calculating a wavefront aberration of the subject eye as optical characteristic on the basis of the measurement data of the first signal from the first light reception unit, a measurement result judgment unit for judging whether the wavefront aberration obtained by the calculation part is appropriate, a second correction unit for causing a check correction screen to be displayed when the measurement result judgment unit judges that a measurement result is inappropriate and for correcting it into appropriate measurement data, and a display unit for displaying the wavefront aberration as a calculation result of the calculation unit.

According to third solving means of the invention, an eye characteristic measuring apparatus includes a light source unit for emitting a light flux with a first wavelength, a first illumination optical system for illuminating a small area on a retina of a subject eye with the light flux from the light source unit, a first light reception optical system for leading a part of a first reflected light flux reflected by and returning from the retina of the subject eye to be received through a first conversion member for converting it into at least substantially 17 beams, a first light reception unit for receiving the received light flux of the first light reception optical system to form a first signal, a measurement data judgment unit for judging, on the basis of the first signal from the first light reception unit, whether measurement data is appropriate for obtaining a wavefront aberration, a first correction unit for causing a check correction screen to be displayed when the measurement data judgment unit judges that the measurement data is inappropriate and for correcting it into appropriate measurement data, a calculation unit for calculating the wavefront aberration of the subject eye as optical characteristic on the basis of the measurement data which has been judged to be appropriate by the measurement data judgment unit or the measurement data which has been corrected by the first correction unit, a measurement result judgment unit for judging whether the wavefront aberration obtained by the calculation part is appropriate, a second correction unit for causing the check correction screen to be displayed when the measurement result judgment unit judges that a measurement result is inappropriate and for correcting it into appropriate measurement data, and a display unit for displaying the wavefront aberration as a calculation result of the calculation unit.

According to fourth solving means of the invention, an eye characteristic measuring apparatus includes a light source unit for emitting a light flux with a first wavelength, a first illumination optical system for illuminating a small area on a retina of a subject eye with the light flux from the light source unit, a first light reception optical system for leading a part of a first reflected light flux reflected by and returning from the retina of the subject eye to be received through a first conversion member for converting it into at least substantially 17 beams, a first light reception unit for receiving the received light flux of the first light reception optical system to form a first signal, a peak extraction unit for extracting a peak of a spot image on the basis of the first signal from the first light reception unit;

a lattice point determination unit for determining a lattice point in a first mode in which a column number of the lattice point is determined from a vicinity of a center axis in a horizontal direction on the basis of the peak of the spot image extracted by the peak extraction unit, and then a row number is determined on the basis of a position of the spot image of the determined column number;

a calculation unit for calculating a wavefront aberration of the subject eye as optical characteristic on the basis of the lattice point determined by the lattice point determination unit, and a display unit for displaying the wavefront aberration as a calculation result of the calculation unit.

According to fifth solving means of the invention, an eye characteristic measuring apparatus includes a light source unit for emitting a light flux with a first wavelength, a first illumination optical system for illuminating a small area on a retina of a subject eye with the light flux from the light source unit, a first light reception optical system for leading a part of a first reflected light flux reflected by and returning from the retina of the subject eye to be received through a first conversion member for converting it into at least substantially 17 beams, a first light reception unit for receiving the received light flux of the first light reception optical system to form a first signal, a peak extraction unit for extracting a peak of a spot image on the basis of the first signal from the first light reception unit, a lattice point determination unit for determining one of a row number and a column number of a lattice point from a vicinity of an axis on the basis of the peak of the spot image extracted by the peak extraction unit, and then determining the other of the column number and the row number from the determined one of the numbers on the basis of a position of the spot image, a calculation unit for calculating a wavefront aberration of the subject eye as optical characteristic on the basis of the lattice point determined by the lattice point determination unit, and a display unit for displaying the wavefront aberration as a calculation result of the calculation unit.

BRIEF DESCRIPTION OF THE DRAWINGS

FIGS. 5(a)-5(c) are views showing check correction screens in cases where mode selection buttons are respectively selected.

FIGS. 15(a) and 15(b) are views showing spots when row and column numbers are given to lattice points.

FIG. 20 is an explanatory view (1) of Zernike polynomials.

FIG. 21 is an explanatory view (2) of the Zernike polynomials.

DESCRIPTION OF THE PREFERRED EMBODIMENTS

Hereinafter, embodiments of the invention will be described in detail with reference to the drawings.

1. Optical System

Figure 1:
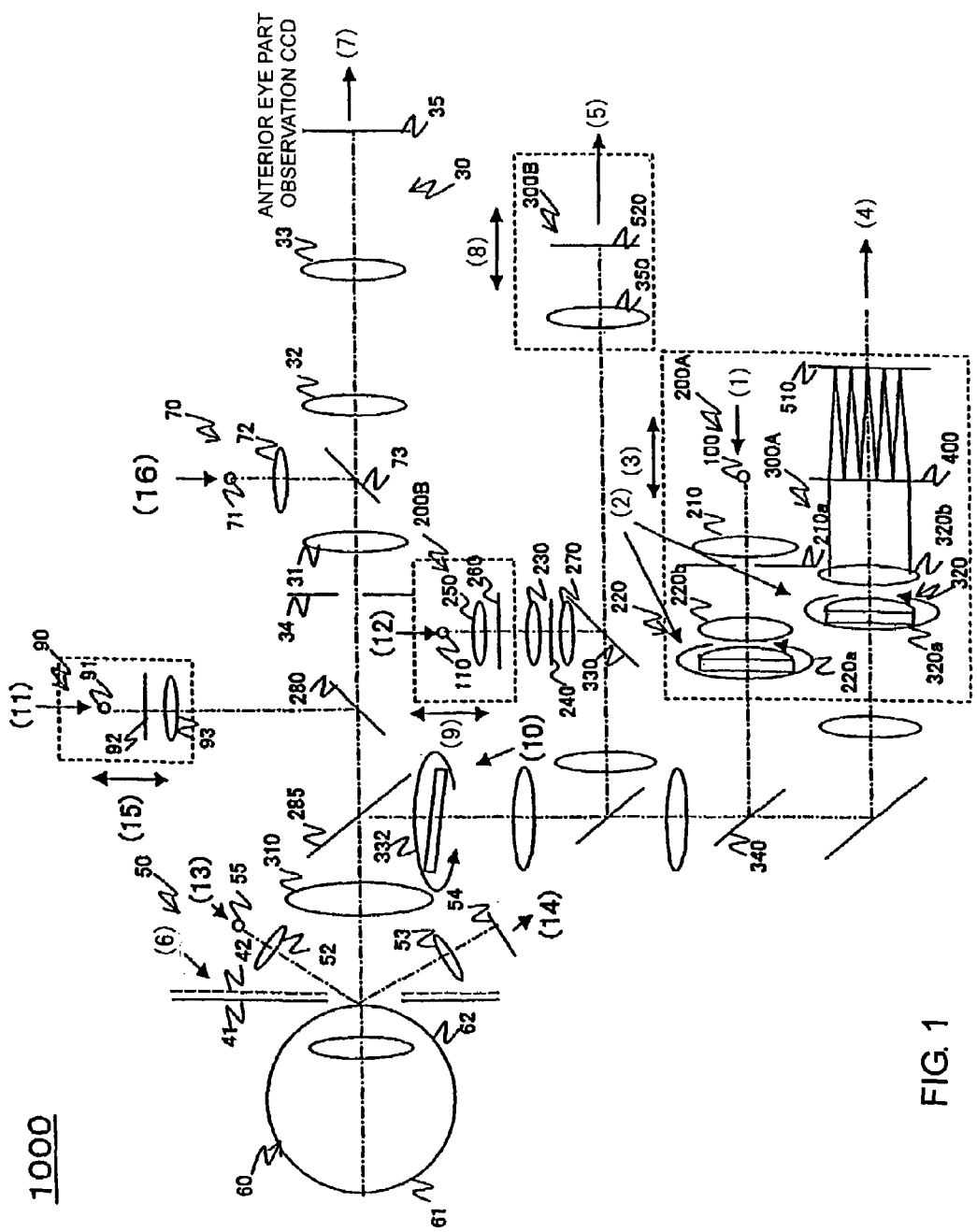
FIG. 1 is a view showing a schematic optical system of an eye characteristic measuring apparatus 1000 of the invention.

FIG. 1 is a view showing a schematic optical system of an eye characteristic measuring apparatus 1000 of the invention.

The eye characteristic measuring apparatus 1000 includes, for example, a first light source unit 100, a first illumination optical system 200A, a first light reception optical system 300A, a first light reception unit 510, a third light source unit 91, a second light source unit 110, a second illumination optical system 200B, a second light reception optical system 300B, a second light reception unit 520, a third light reception optical system 30, a first adjusting optical system 50, a second adjusting optical system 70, and a third illumination optical system 90. With respect to an eye 60 to be measured, a retina (fundus) 61 and a cornea (anterior eye part) 62 are shown in the drawing.

The first light source unit 100 emits a light flux with a first wavelength. The first illumination optical system 200A illuminates a small area on the retina 61 of the subject eye with the first light flux from the first light source unit 100. The first light reception optical system 300A leads, for example, a part of a light flux reflected by and returning from the retina 61 of the subject eye to a first light reception unit 510 through a first conversion member 400 for converting the reflected light flux into at least 17 beams. The second light source unit 110 emits a light flux with a second wavelength. The second illumination optical system 200B illuminates a predetermined area on the retina 61 of the subject eye with the second light flux from the second light source unit 110. The second light reception optical system 300B leads the second light flux reflected by and returning from the retina 61 of the subject eye to the second light reception part 520.

Hereinafter, the respective units will be described in detail.

The first illumination optical system 200A is for illuminating a small area on the retina 61 of the subject eye with, for example, the light flux from the first light source unit 100. The first illumination optical system 200A includes a first light converging lens 210, a first pair of positive and negative cylinder lenses (so-called variable cross-cylinder) 220a, and a first relay lens 220b.

It is desirable that the first light source unit 100 has high spatial coherence and not high temporal coherence. Here, as an example, an SLD is adopted as the first light source unit 100, and a point light source with high brightness can be obtained. Incidentally, the first light source unit 100 is not limited to the SLD, and even if both the spatial and temporal coherences are high like a laser, it can be used by inserting a rotation diffused plate or the like to properly lower the temporal coherence. Then, even if both the spatial and temporal coherences are not high like the LED, if only the quantity of light is sufficient, it can be used by inserting a pinhole or the like at a position of a light source in an optical path. Besides, as the wavelength of the first light source unit 100 for illumination, for example, a wavelength in an infrared range, for example, 780 nm can be used.

The first light reception optical system 300A is for receiving, for example, the light flux reflected by and returning from the retina 61 of the subject eye and having passed through a second beam splitter 340 and for leading it to the first light reception unit 510. The first light reception optical system 300A includes a first afocal lens 310, a second pair of positive and negative cylinder lenses (so-called variable cross-cylinder) 320a, a second relay lens 320b, the second beam splitter 340, and the conversion member 400 for converting the reflected light flux into at least 17 beams.

The conversion member 400 disposed in the first light reception optical system 300A is a wavefront conversion member for converting the reflected light flux into plural beams. Incidentally, here, plural micro-Fresnel lenses disposed on a plane orthogonal to the optical axis are adopted as the conversion member 400.

The first light reception unit 510 is for receiving the light having passed through the conversion member 400 and from the first light reception optical system 300A and for generating a first signal. With respect to the first light reception unit 510, the first light source unit 100 and the retina 61 are conjugated with each other, and the retina 61 and the first light reception unit 510 are conjugated with each other. Further, the conversion member 400 and the pupil are also conjugated with each other. That is, the front focal point of the first afocal lens 310 is substantially coincident with the anterior eye part 62 of the subject eye 60 as the object to be examined. The reflected light from the retina 61 passes through the first afocal lens 310 and the second variable cross-cylinder 320, and is converged on the first light reception unit 510 through the conversion member 400.

Then, the first illumination optical system 200A and the first light reception optical system 300A are moved in synchronization with each other, while on the assumption that the light flux from the first light source unit 100 is reflected at a converged point, such a relation that the signal peak at the first light reception unit 510 by the reflected light becomes maximum is kept, and they are moved in a direction in which the signal peak at the first light reception unit 510 becomes high, and are stopped at the position where the intensity becomes maximum.

The first converging lens 210 converts diffused light of the first light source unit 100 into parallel light. A lens stop 210a is placed at a position where it is optically conjugated with the pupil of the subject eye 60 or the conversion member (Hartmann plate) 400. The diameter of the lens stop 210a is smaller than the effective range of the Hartmann plate 400, and a so-called single path aberration measurement (method in which aberration of an eye has an influence on only a light reception side) is established. The first relay lens 220b is disposed such that an retina conjugated point of a real light beam is coincident with the front focal point position in order to satisfy the above, and the rear focal point position is coincident with the lens stop 210a in order to satisfy the conjugated relation to the pupil of the eye.

After the incident light beam emitted from the first light source unit 100 comes to have an optical path common to the measurement light beam diffused and reflected from the retina 61 through the second beam splitter 340, it paraxially advances in the same way as the measurement light beam diffused and reflected from the retina 61. However, at the single path measurement, the diameters of the respective light beams are different from each other, and the beam diameter of the incident light beam is set to be rather thin as compared with the measurement light beam. Specifically, the beam diameter of the incident light beam is, for example, about 1 mm at the pupil position of the subject eye 60, and the beam diameter of the measurement light beam becomes about 7 mm.

The second illumination optical system 200B is for illuminating a specified area on the retina of the subject eye with the second light flux from the second light source unit 110. The second light source unit 110 is for emitting the light flux with the second wavelength of, for example, 860 nm. The second illumination optical system 200B includes, for example, the second light source unit 110, a third converging lens 230, a first ring stop 240, a fourth converging lens 250, a second ring stop 260, a lens 270, and a first beam splitter 330. The third converging lens 230 and the first ring stop 240 are for illuminating the pupil, and the fourth converging lens 250 and the second ring stop 260 are for illuminating the retina 61.

The second light reception optical system 300B includes, for example, the first afocal lens 310, the first beam splitter 330, and a second converging lens 350. The light with the second wavelength reflected by a beam splitter 285 formed between the first afocal lens 310 and the first beam splitter 330 is led to the second light reception unit 520 through the first beam splitter 330 and the second converging lens 350. The second light reception unit 520 generates a second signal.

The beam splitter 285 is constructed of, for example, a dichroic mirror which reflects the light flux with the first wavelength. A rotary prism 332 for uniforming the light subjected to uneven reflection or the like from the retina 61 is disposed between the second beam splitter 340 and the beam splitter 285. The rotary prism 332 is substantially conjugated with the pupil.

The first light source unit 100, the second ring stop 260 equivalent to the secondary light source of the second light source unit 110, and the retina 61 are conjugated with each other, and the retina 61, the first light reception unit 510 and the second light reception unit 520 are conjugated with each other. Further, the conversion member 400 and the pupil are also conjugated with each other, and the pupil and the first ring stop 240 are conjugated with each other.

The third light reception optical system 30 includes relay lenses 31, 32 and 33, a telecentric stop 34, and a third light reception unit (here, for example, an anterior eye part observation CCD) 35. The third light reception optical system 30 leads a light flux, which is formed such that a pattern of a Placido ring 41 illuminated from a light source unit 42 for a Placido ring included in the first adjusting optical system 50 is reflected by and returns from the anterior eye part 62 of the eye 60 to be measured, to the third light reception unit 35. Besides, the telecentric stop 34 is, for example, a stop for preventing the anterior eye image from blurring. A beam splitter 280 is disposed between the telecentric stop 34 and the beam splitter 285. Incidentally, instead of the Placido ring 41, for example, a keratoring may be used, and in this case, a pattern of only the vicinity of the center of curvature of the cornea 62 can be obtained by a kerato image.

The first adjusting optical system 50 is for, for example, mainly performing a working distance adjustment, and includes a light source unit 55, converging lenses 52 and 53, and a light reception unit 54. Here, the working distance adjustment is performed such that, for example, a parallel light flux emitted from the light source unit 55 and close to the optical axis is irradiated to the eye 60 to be measured, and the light reflected by the eye 60 to be measured is received by the light reception unit 54 through the converging lenses 52 and 53. Besides, in the case where the eye 60 to be measured is in a suitable working distance, a spot image from the light source unit 55 is formed on the optical axis of the light reception unit 54. On the other hand, in the case where the eye 60 to be measured falls outside the suitable working distance, the spot image from the light source unit 55 is formed above or below the optical axis of the light reception unit 54. Incidentally, since the light reception unit 54 has only to detect a change in light flux position on a plane including the light source unit 55, the optical axis and the light reception unit 54, for example, a one-dimensional CCD disposed on this plane, a position sensing device (PSD) or the like can be applied.

The second adjusting optical system 70 is for performing, for example, an alignment adjustment in the XY direction, and includes a light source unit 71 for alignment, a lens 72, and a beam splitter 73.

The third illumination optical system 90 includes an optical path for projection of, for example, an index to cause fixation of the subject eye or fogging, and includes the third light source unit (for example, lamp) 91, a fixation index 92, and a relay lens 93. The fixation index 92 can be irradiated toward the retina 61 by the light flux from the third light source unit 91, and the subject eye 60 is made to observe its image.

2. Eye Characteristic Measuring Apparatus (I)

Figure 2:
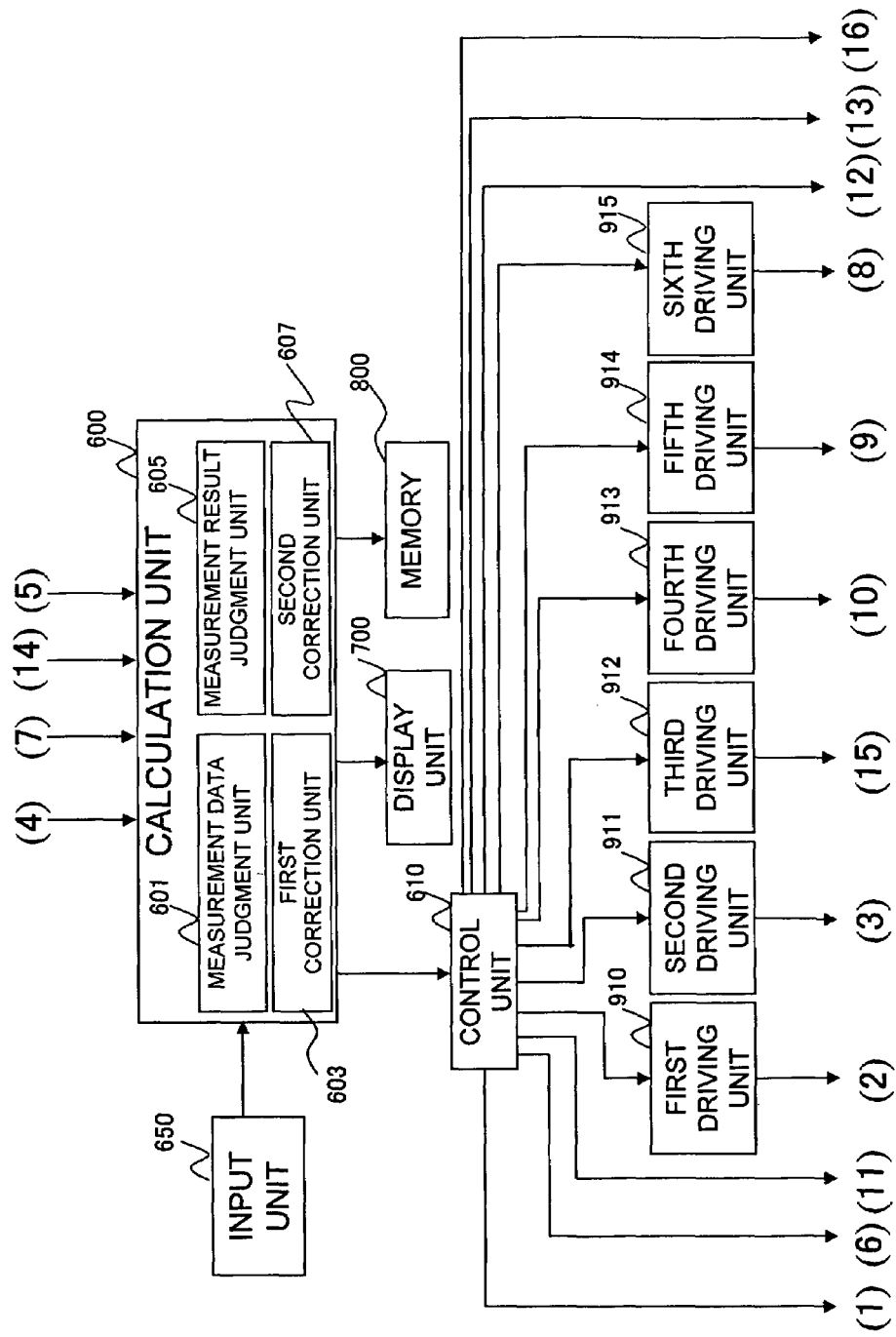
FIG. 2 is an electrical system block diagram showing an electric structure of the eye characteristic measuring apparatus 1000 of the invention.

FIG. 2 is an electrical block diagram showing an electric structure of the eye characteristic measuring apparatus 1000 of the invention.

The electric driving system of the eye characteristic measuring apparatus 1000 includes a calculation unit 600, a control unit 610, an input unit 650, a display unit 700, a memory 800, a first driving unit 910, a second driving unit 911, a third driving unit 912, a fourth driving unit 913, a fifth driving unit 914, and a sixth driving unit 915. The calculation unit 600 includes, for example, a measurement data judgment unit 601, a first correction unit 603, a measurement result judgment unit 605, a second correction unit 607, and a measurement unit for performing various eye characteristic measurements. Further, the input unit 650 includes a pointing device for indicating a suitable button disposed on the display unit 700, an icon, a position, an area and the like, a keyboard for inputting various data, and the like.

The calculation unit 600 is constructed such that a first signal (4) from the first light reception unit 510, a second signal (5) from the second light reception unit 520, a signal (7) from the third light reception unit 35, and a signal (14) from the light reception unit 54 are inputted. The calculation unit 600 obtains the optical characteristic of the subject eye 60 on the basis of the first signal (4) from the first light reception unit 510, calculates a refractive power, a degree of astigmatism, and an astigmatic axis angle and detects the illumination state of the first illumination optical system 200A on the basis of the second signal (5) from the second light reception unit 520. Besides, the calculation unit 600 outputs signals corresponding to the calculation results to the control unit 610 for controlling the whole of the electric driving system, the display unit 700 (various display examples will be described later) and the memory 800. Incidentally, the calculation unit 600 obtains the optical characteristic of the subject eye 60 on the basis of, for example, the first signal from the first light reception unit 510 corresponding to the tilt angle of a light flux.

The measurement data judgment unit 601 judges whether measurement data is appropriate for obtaining the wavefront aberration on the basis of, for example, the first signal from the first light reception unit 510 (on the basis of the tilt angle of the light flux obtained by the first light reception unit 510). For example, when the measurement data judgment unit 601 judges that the measurement data is inappropriate, the first correction unit 603 causes an after-mentioned check correction screen to be displayed, and corrects it into appropriate measurement data.

The calculation unit 600 calculations the wavefront aberration of the subject eye 60 as optical characteristic on the basis of the measurement data which has been judged to be appropriate by the measurement data judgment unit 601 or the measurement data which has been corrected by the first correction unit 603. The measurement result judgment unit 605 judges whether for example, the wavefront aberration obtained by the calculation unit 600 is appropriate. For example, when the measurement result judgment unit 605 judges that a measurement result is inappropriate, the second correction unit 607 causes a check correction screen to be displayed and corrects it into appropriate measurement data.

The control unit 610 is for controlling to switch on and off the first light source unit 100 and for controlling the first driving unit 910 to the sixth driving unit 915 on the basis of the control signals from the calculation unit 600. The control unit 610 outputs a signal (1) to the first light source unit 100 on the basis of the signal corresponding to the calculation result of the calculation unit 600, outputs a signal (12) to the second light source unit 110, outputs a signal (11) to the third light source unit 91, outputs a signal (13) to the light source unit 55, outputs a signal (16) to the light source unit 71 for alignment, outputs a signal (6) to the light source unit 42 for the Placido ring, and outputs signals to the first driving unit 910 to the sixth driving unit 915.

The first driving unit 910 outputs a signal (2) on the basis of the signal (4) inputted to the calculation unit 600 from the first light reception unit 510 and for rotating the first variable cross-cylinder 220a of the first illumination optical system 200A and the second variable cross-cylinder 320a of the first light reception optical system 300A. The first driving unit 910 drives suitable lens movement means, rotates the first cylinder lens 220a, and corrects the astigmatism component of the subject eye. Incidentally, the two variable cross-cylinders may not be provided, and this correction may not be preformed.

The second driving unit 911 is for moving, for example, the first illumination optical system 200A and the first light reception optical system 300A in the optical axis direction on the basis of the light reception signal (4) inputted to the calculation unit 600 from the first light reception unit 510, outputs a signal (3) to not-shown suitable lens movement means and drives this lens movement means.

The third drive unit 912 is for moving, for example, the fixation index 92 of the third illumination optical system 90, outputs a signal (15) to not-shown suitable movement means, and drives this movement means. By this, the third drive unit 912 can move and adjust the fixation index 92 of the third illumination optical system 90.

The fourth driving unit 913 is for rotating, for example, the rotary prism 332, outputs a signal (10) to not-shown suitable lens movement means and drives this lens movement means.

The fifth driving unit 914 is for moving, for example, the second illumination optical system 200B in the optical axis direction on the basis of the signal (12) outputted from the calculation unit 600 to the second light source unit 110, outputs a signal (9) to not-shown suitable lens movement means, and drives this lens movement means.

The sixth driving unit 915 is for moving, for example, the second light reception optical system 300B in the optical axis direction on the basis of the light reception signal (5) inputted to the calculation unit 600 from the second light reception unit 520, outputs a signal (8) to not-shown suitable lens movement means, and drives this lens movement means.

Flowchart of First Embodiment

Figure 3:
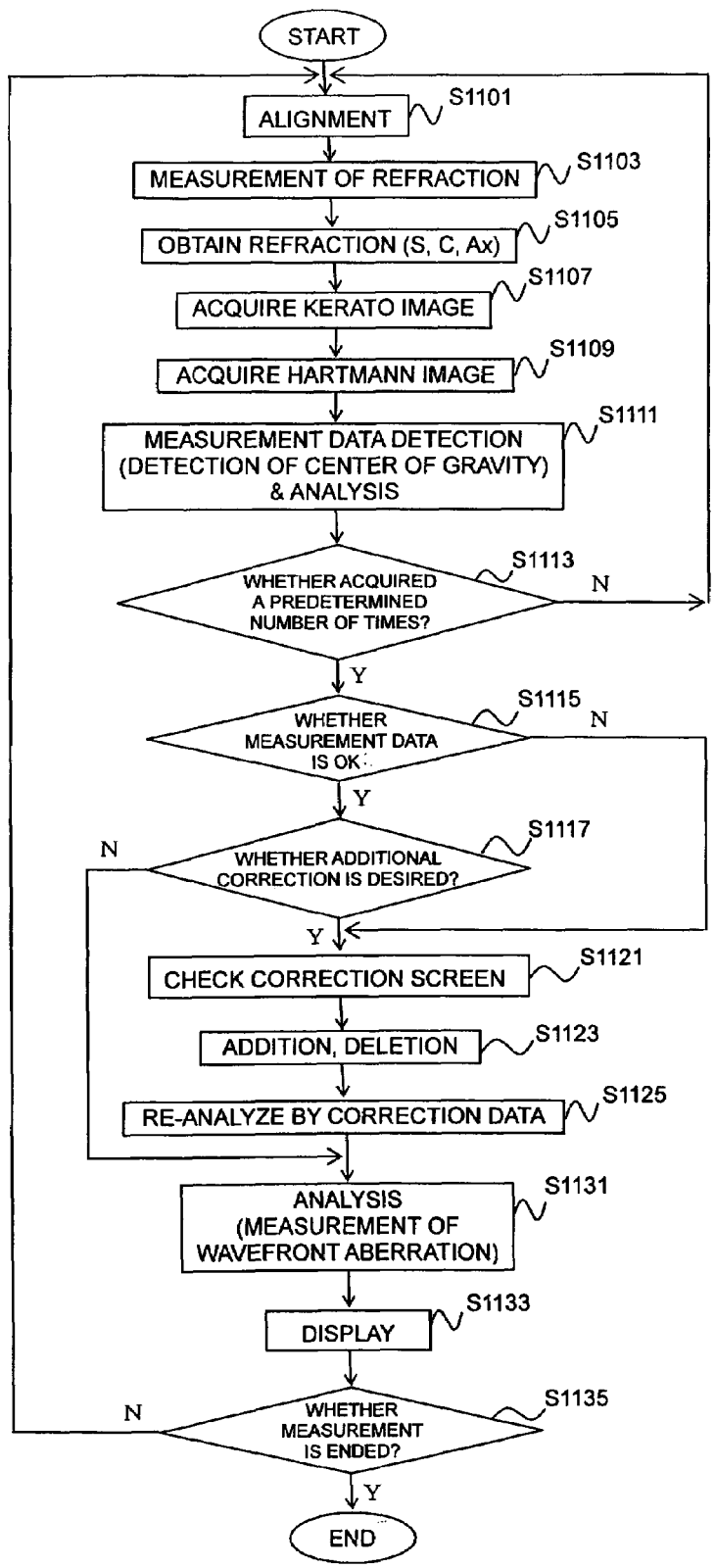
FIG. 3 is a flowchart of a first embodiment showing a specific measurement method of the eye characteristic measuring apparatus 1000.

FIG. 3 is a flowchart of a first embodiment showing a specific measurement method of the eye characteristic measuring apparatus 1000. The flowchart shows a processing in which before the wavefront aberration is displayed, it is judged whether data is appropriate for analysis, and when it is inappropriate, a check correction screen is automatically displayed or is displayed by the instruction of a checker, and after correction, the wavefront aberration is calculated and is displayed.

When a measurement is started, first, the alignment adjustment of the position of the subject eye 60 is performed (S1101). Here, for example, in accordance with the instruction of the checker, the control unit 610 controls a specified driving unit on the basis of the control signal from the calculation unit 600, performs the alignment, and puts the subject eye 60 and the optical system of the eye characteristic measuring apparatus 1000 into a suitable arrangement.

Next, after the alignment adjustment, the calculation unit 600 measures refractions by an auto refract meter (S1103). The calculation unit 600 obtains the refractions such as a refractive power, a degree of astigmatism, and an astigmatic axis angle (S, C, Ax) on the basis of the measurement at step S1103 (S1105). After step S1105, the calculation unit 600 obtains a kerato image by the third light reception unit 35 of the third light reception optical system 30 (S1107). Incidentally, at step S1107, although the kerato image is used, instead thereof, a Placido ring image may be acquired. Further, the calculation unit 600 acquires a Hartmann image by the first light reception unit 510 of the first light reception optical system 300A (S1109).

The calculation unit 600 performs detection of measurement data (for example, detection of the center of gravity of each spot of the Hartmann image) and analysis of eye optical characteristics such as the wavefront aberration (S1111). Even if this analysis is not ended, the Hartmann image can be acquired a predetermined number of times. Next, the calculation unit 600 judges whether the measurement data detected at step S1111 is acquired a predetermined number of times (S1113). In the case where it is not acquired the predetermined number of times, the procedure returns to step S1101 again, and the processing subsequent to the alignment adjustment is performed.

On the other hand, in the case where the measurement data is acquired the predetermined number of times at step S1113, the measurement data judgment unit 601 judges whether the measurement data is appropriate for analysis (measurement of the eye optical characteristics such as the wavefront aberration) (S1115). The measurement data judgment unit 601 can judge the propriety of the measurement data at step S1115 by one of or a combination of following conditions.

Whether the total density of spot images is a predetermined value or higher?

Whether the number of extracted spots is a predetermined number or higher?

Whether the level of spot images is a predetermined level or higher?

In the case where the measurement data judgment unit 601 judges at step S1115 that the measurement data is appropriate, the calculation unit 600 judges whether the proper checker desires an additional correction (S1117). In the case where the checker does not desire the addition correction at step S1117, the calculation unit 600 performs an analysis of step S1131.

On the other hand, in the case where the measurement data judgment unit 601 judges at step S1115 that the measurement data is inappropriate for the analysis, the first correction unit 603 automatically displays a check correction screen on the display unit 700, and proceeds to a confirmation correction mode (S1121). This check correction screen is also displayed in the case where the checker desires the additional correction at step S1117, and the procedure proceeds to the confirmation correction mode.

Here, the confirmation correction mode will be described.

Figure 4:
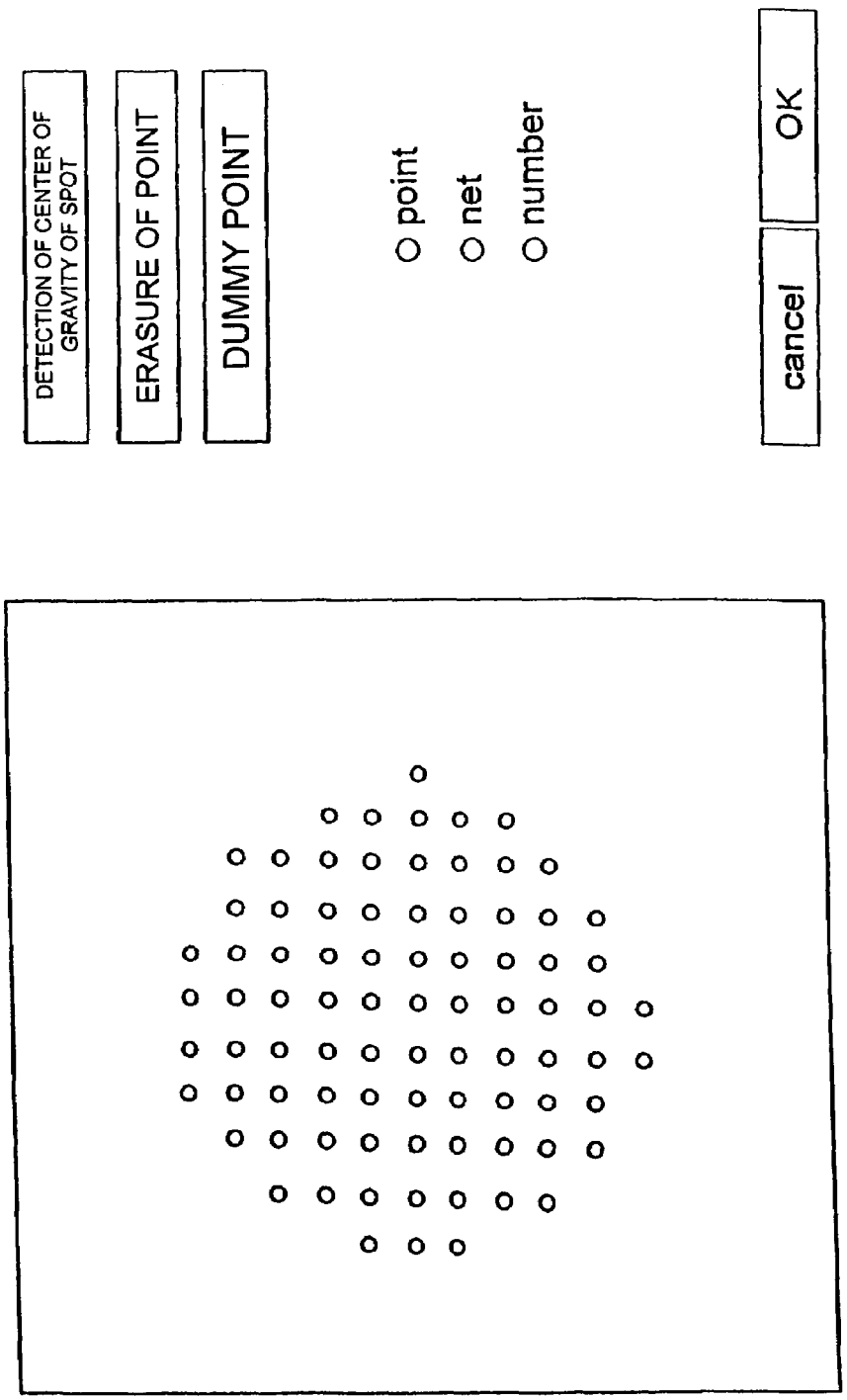
FIG. 4 is a view showing a display example of a check correction screen.

FIG. 4 is a view showing a display example of the check correction screen.

On the check correction screen, for example, respective spots (in the drawing, marks O) of the Hartmann image are displayed. The check correction screen includes, for example, a "point" mode in which the center of gravity of each spot is denoted by +, a "net" mode indicating a state where the respective spots are connected to each other like a lattice, and a "number" mode indicating a state where a suitable coordinate value is given to each spot, and includes mode selection buttons ("point", "net", "number") for selecting these modes. These modes can be duplicately selected and displayed. Besides, the check correction screen further includes execution buttons for executing after-mentioned "detection of center of gravity of spot", "erasure of point", and "dummy point (addition of dummy point)".

Next, on the check correction screen, cases where these mode selection buttons ("point", "net", "number") are respectively selected in accordance with the instruction of the checker, will be described specifically.

FIG. 5 is a view showing check correction screens in the cases where the mode selection buttons are respectively selected.

First, FIG. 5(a) shows a state where the "point" mode is selected. FIG. 5(b) shows a state where the "net" mode is selected. FIG. 5(c) shows a state where the "number" mode is selected.

Here, a return is made to FIG. 3 again and a description will be made. The first correction unit 603 performs addition and deletion of spots on the check correction screen (S1123). Hereinafter, step S1123 will be described.

Figure 6:
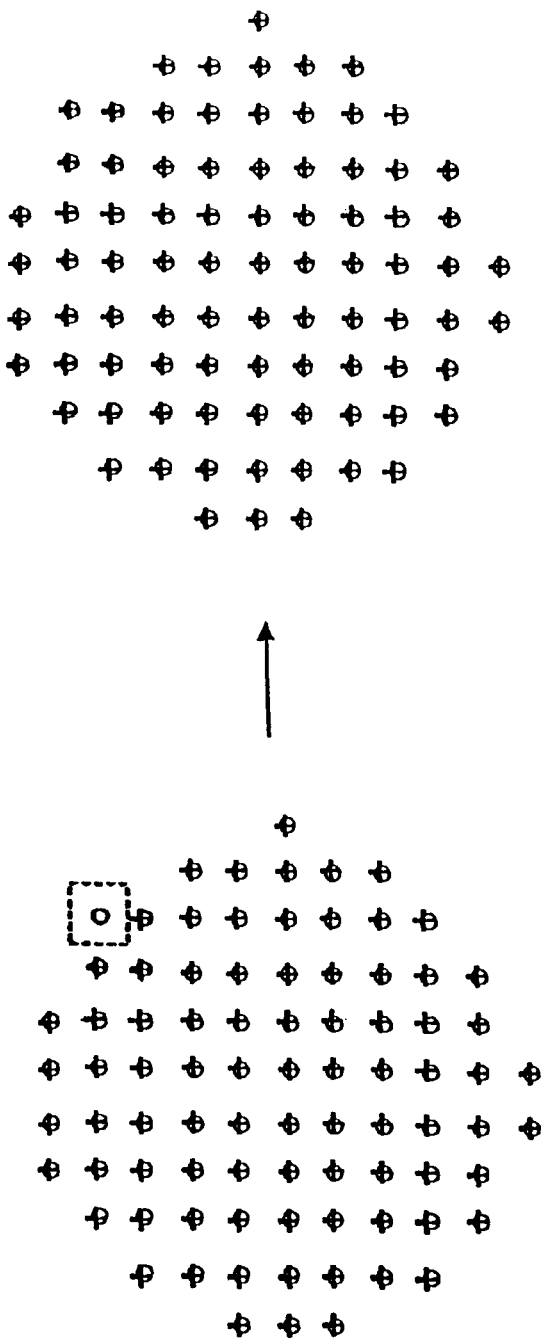
FIG. 6 is a view showing a case where an execution button "detection of center of gravity of spot" on the check correction screen is selected.

FIG. 6 is a view showing a case where the execution button "detection of center of gravity of spot" on the check correction screen is selected.

As the processing of step S1123, for example, in the case where the execution button "detection of center of gravity of spot" is selected on the check correction screen, when an area to which addition of the center of gravity of a spot is desired is selected by the proper checker using the input unit 650 such as a pointing device or a keyboard, the first correction unit 603 detects the center of gravity of the spot. In order to surround the area to which the addition of the center of gravity of the spot is desired, for example, a mouse pointer is moved on a diagonal line of a rectangle, an ellipse or the like, or it is surrounded by a free curved line. Incidentally, in the detection of the center of gravity of the spot, the center of gravity can be detected by changing the threshold of light quantity level at the time when the spot is extracted in the area including all the spots. For example, in the detection of the center of gravity of the spot, for example, an area where a blur of each spot is included is surrounded by a rectangle, an ellipse or the like, the whole shading is also consider, for example, the background of shading, and noise components are removed, so that the center of gravity of the spot can be detected (shading correction). Although the detection of the center of gravity is performed at one point for each area in this case, it is also possible to make such setting that detection is performed at plural points in the area.

Figure 7:
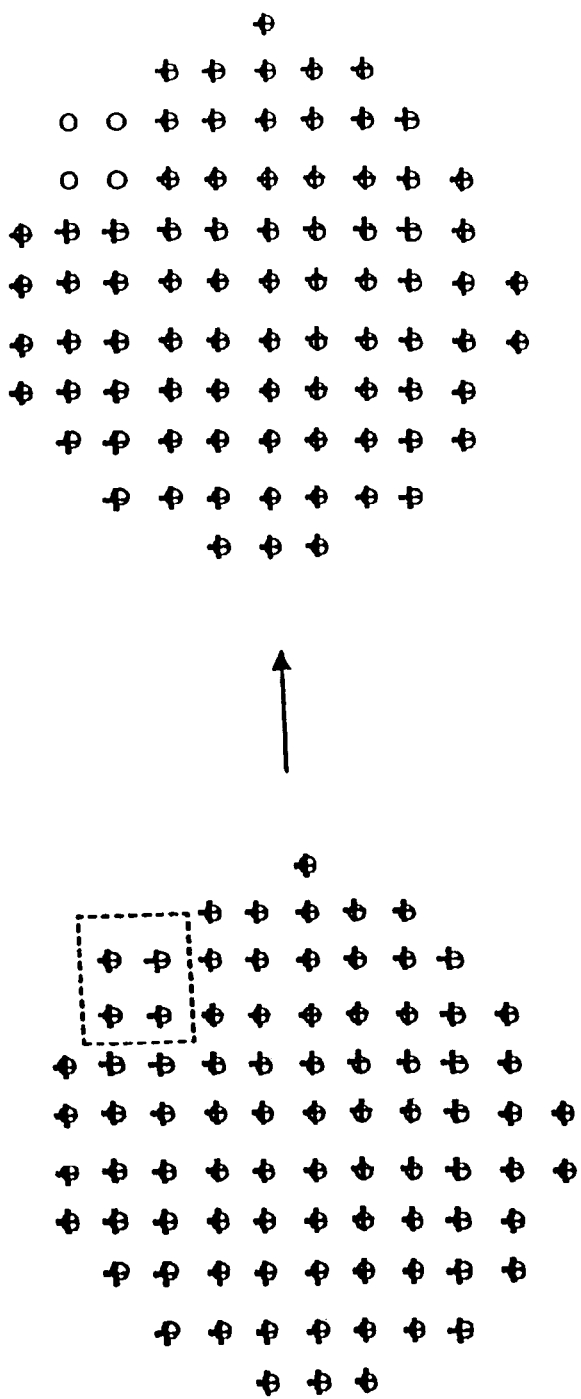
FIG. 7 is a view showing a case where an execution button "erasure of point" on the check correction screen is selected.

FIG. 7 is a view showing a case where the execution button "erasure of point" on the check correction screen is selected.

As the processing of step S1123, for example, in the case where the execution button "erasure of point" is selected on the check correction screen, when an area where deletion of the center of gravity of a spot is desired is selected by the proper checker using the input unit 650 such as the pointing device or the keyboard, the first correction unit 603 detects it, and deletes the center of gravity of the spot in the area. Here, in order to delete the center of gravity of the spot, the area including the center of gravity of the spot, the deletion of which is desired, can be surrounded by the same method as that of the case where the foregoing detection of the center of gravity of the spot is performed.

FIG. 8 is a view showing a case where the execution button "dummy point" on the check correction screen is selected.

Figure 8C:
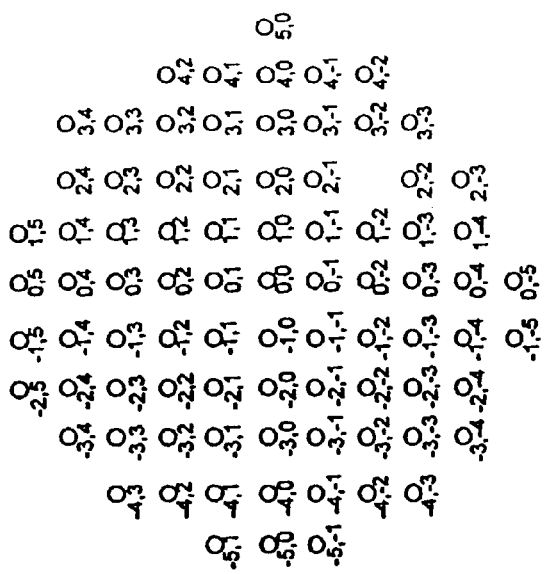
FIGS. 8(a)-8(c) are views showing a case where an execution button "dummy point" on the check correction screen is selected.
Figure 8B:
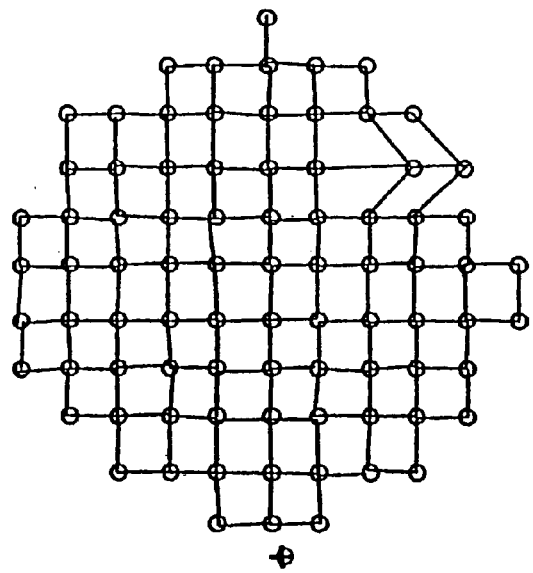
Figure 8A:
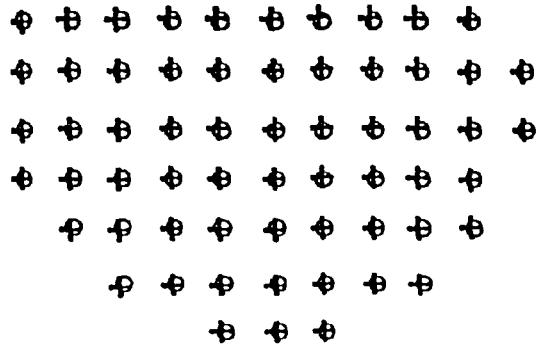

First, FIG. 8(a) shows a state where the "point" mode is selected. Here, a spot is not extracted in an area A. Thus, the measurement data judgment unit 601 judges at step S1115 that the measurement data is inappropriate. FIG. 8(b) shows a state where the "net" mode is selected. Here, since the spot is not extracted in the area A of FIG. 8(a), the correspondence of the lattice in the vicinity of the area A is erroneous. Besides, FIG. 8(c) shows a state where the "number" mode is selected. Here, since the spot is not extracted in the area A of FIG. 8(a), the coordinate values of spots in the vicinity of the area A are given while the area A is skipped.

Here, in order to perform the correspondence with the correct lattice point, as the processing of step S1123, for example, in the case where the execution button "dummy point" is selected on the check correction screen, when a place (for example, a point contained in the area A) to which addition of the dummy point, which is not used for aberration analysis, is desired, is selected by the proper checker using the input unit 650 such as the pointing device or the keyboard, the first correction unit 603 adds the dummy point to that place. Incidentally, when the dummy point is added to the area A, the respective spots become substantially uniform, and the check correction screens become, for example, the check correction screens of the respective modes shown in FIG. 5.

Here, a return is made to FIG. 3 again and a description will be made. After the "OK" button is pressed, the calculation unit 600 performs re-analysis (S1125) on the basis of the corrected data in which the addition or deletion has been made at step S1123, and performs analysis (measurement of eye optical characteristic such as wavefront aberration) (S1131). In the case where the "Cancel" button is pressed, the matters changed in the confirmation correction mode are neglected, and the automatically detected original analysis result is used.

After performing the analysis at step S1131, the calculation unit 600 displays various display objects on the display unit 700 (S1133). The display objects include, for example, a center of gravity/lattice map as an retinal image, a keratoring or a Placido ring extracted as a corneal image, a pupil edge, a wavefront measurement value, an anterior eye image, a Hartmann image, a refraction, a wavefront aberration and the like.

Next, after performing the display at step S1133, the calculation unit 600 judges whether the measurement is to be ended (S1135), and in the case where the measurement is to be ended, the measurement is ended. On the other hand, in the case where the measurement is not to be ended at step S1135, a return is made to step S1101 again, and the alignment adjustment is performed.

Flowchart of Second Embodiment

Figure 9:
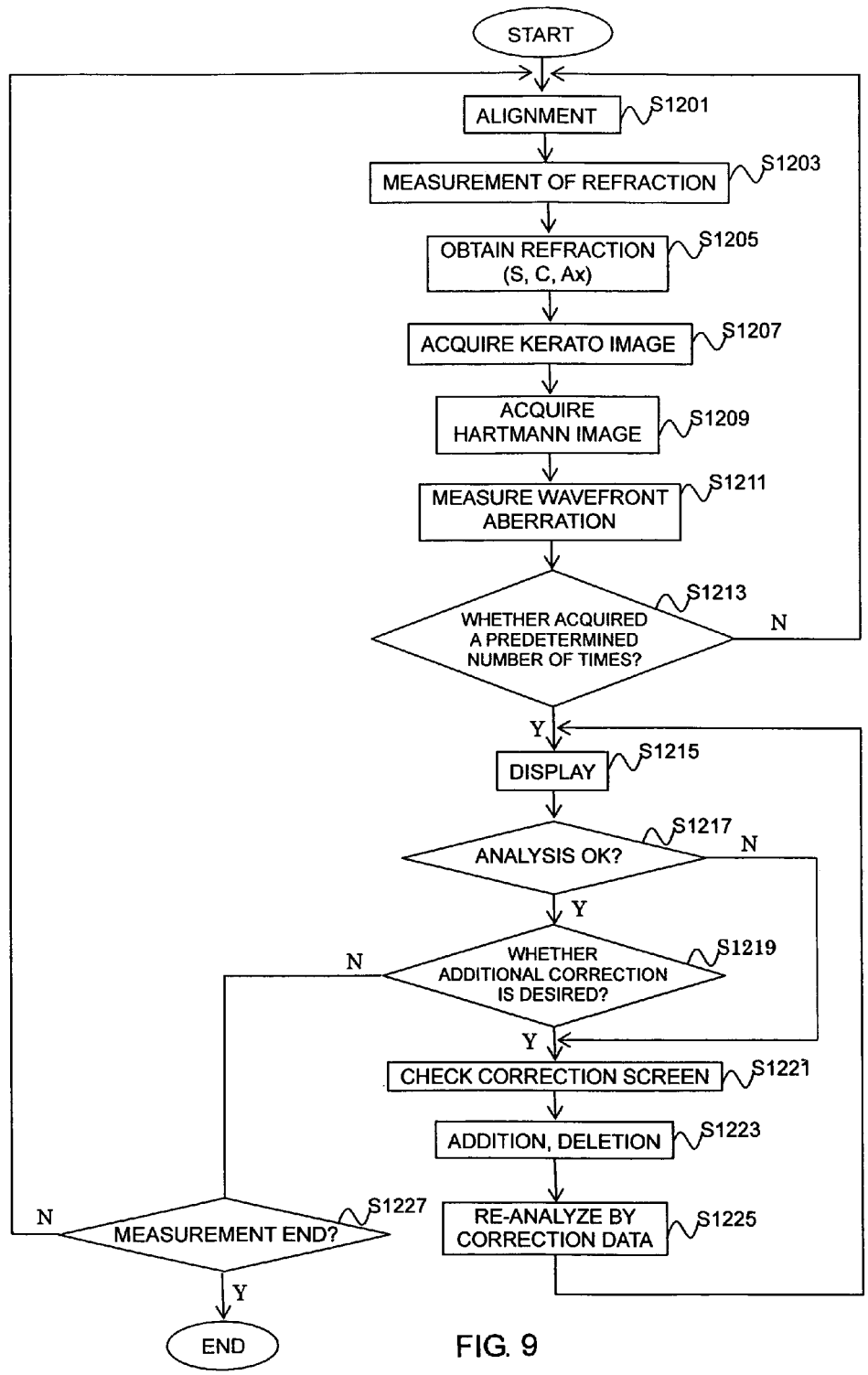
FIG. 9 is a flowchart of a second embodiment showing a specific measurement method of the eye characteristic measuring apparatus 1000.

FIG. 9 is a flowchart of a second embodiment showing a specific measurement method of the eye characteristic measuring apparatus 1000. Incidentally, processings overlapping with those of the foregoing flowchart will be described to such a degree that redundancy does not occur. The flowchart here shows such a processing that the calculation and display of the wavefront aberration are performed, and then, it is judged whether an analysis result has been appropriate, and in the case where the analysis result has been inappropriate, a check correction screen is displayed or displayed by the instruction of a checker, and after correction, the wavefront aberration is calculated and the display is performed.

When the measurement is started, first, the alignment adjustment of the position of the subject eye 60 is performed (S1201). After the alignment adjustment, the calculation unit 600 measures refractions by an auto refract meter (S1203). The calculation unit 600 obtains refractions such as a refractive power, a degree of astigmatism, and an astigmatic axis angle (S, C, Ax) on the basis of the measurement at step S1203 (S1205). The calculation unit 600 acquires a kerato image or a Placido ring image by the third light reception unit 35 of the third light reception optical system 30 (S1207), and further acquires a Hartmann image by the first light reception unit 510 of first light reception optical system 300A (S1209).

Next, the calculation unit 600 performs an analysis (measurement of optical characteristic such as wavefront aberration) (S1211), and judges whether the analysis data detected at step S1211 is acquired a predetermined number of times (S1213). Incidentally, even if the analysis is not ended, the Hartmann image can be acquired the predetermined number of times. In the case where it is not acquired the predetermined number of times, a return is made to step S1201 again, and the alignment adjustment is performed. On the other hand, in the case where the measurement data is acquired the predetermined number of times at step S1213, the calculation unit 600 displays the analysis result at step S1211 on the display unit 700 (S1215). The Hartmann image similar to that of the confirmation correction mode of the flowchart of the first embodiment, and a display including only the display buttons of "Point", "Net", "Number" are also simultaneously displayed. The measurement result judgment unit 605 judges whether the analysis result at step S1211 is appropriate (S1217).

The measurement result judgment unit 605 can judge the propriety of the analysis result by one of or a combination of following conditions, for example, at step S1217.

Whether a component of a defocus term ($Z_2^0$, described later) of Zernike coefficients of wavefront components is close to zero?

Whether Zernike coefficients of an aberration of a cornea of large refractivity and those of a wavefront aberration of the subject eye have the same tendency?

Whether it is similar to the data of a personal medical record (in a database previously measured) when they are compared with each other?

Whether plural newly measured data for the same subject eye are almost equal to each other when they are compared with each other?

Here, the meaning of the Zernike coefficients will be described. For example, $Z_0^0$ denotes a constant term; $Z_1^{-1}$, a tilt term; $Z_1^1$, a tilt term; $Z_2^{-2}$, astigmatism component; $Z_2^0$, refractive power component; $Z_2^2$, astigmatism component; $Z_3^{-3}$, sagittal aberration; $Z_3^{-1}$, third coma aberration; $Z_3^1$, third coma aberration; $Z_3^3$, sagittal aberration; $Z_4^{-2}$, third astigmatism; $Z_4^0$, third spherical aberration; $Z_4^2$, third astigmatism; $Z_5^{-1}$, fifth coma aberration; $Z_5^1$, fifth coma aberration; and $Z_6^0$, fifth spherical aberration. FIGS. 20 and 21 are explanatory views (1) and (2) concerning the Zernike polynomials.

Next, in the case where the analysis result is inappropriate at step S1217, the second correction unit 607 automatically causes the check correction screen to be displayed on the display unit 700, and proceeds to an additional correction mode (S1221). Thereafter, similarly to the confirmation correction mode of the flowchart of the first embodiment, the second correction unit 607 performs the addition/deletion of spots on the check correction screen (S1223). Next, the calculation unit 600 performs re-analysis on the basis of the added/deleted correction data (S1225).

Next, the calculation part 600 displays the analysis result by the re-analysis at step S1225 on the display part 700 (S1215). Incidentally, even if the analysis result is appropriate at step S1217, the calculation unit 600 judges whether the proper checker desires an additional correction (S1219). In the case where the checker desires the additional correction at step S1219, the second correction unit 607 performs the foregoing step S1221. On the other hand, in the case where the additional correction is not desired, the calculation unit 600 judges whether the measurement is to be ended (S1227), and in the case where the measurement is to be ended, the measurement is ended. On the other hand, in the case where the measurement is not to be ended at step S1227, a return is made to step S1201 again, and the processing subsequent to the alignment adjustment is performed. Incidentally, when the analysis result is displayed on the display unit 700 after the measurement end, a re-analysis can also be performed.

Flowchart of Third Embodiment

Figure 10:
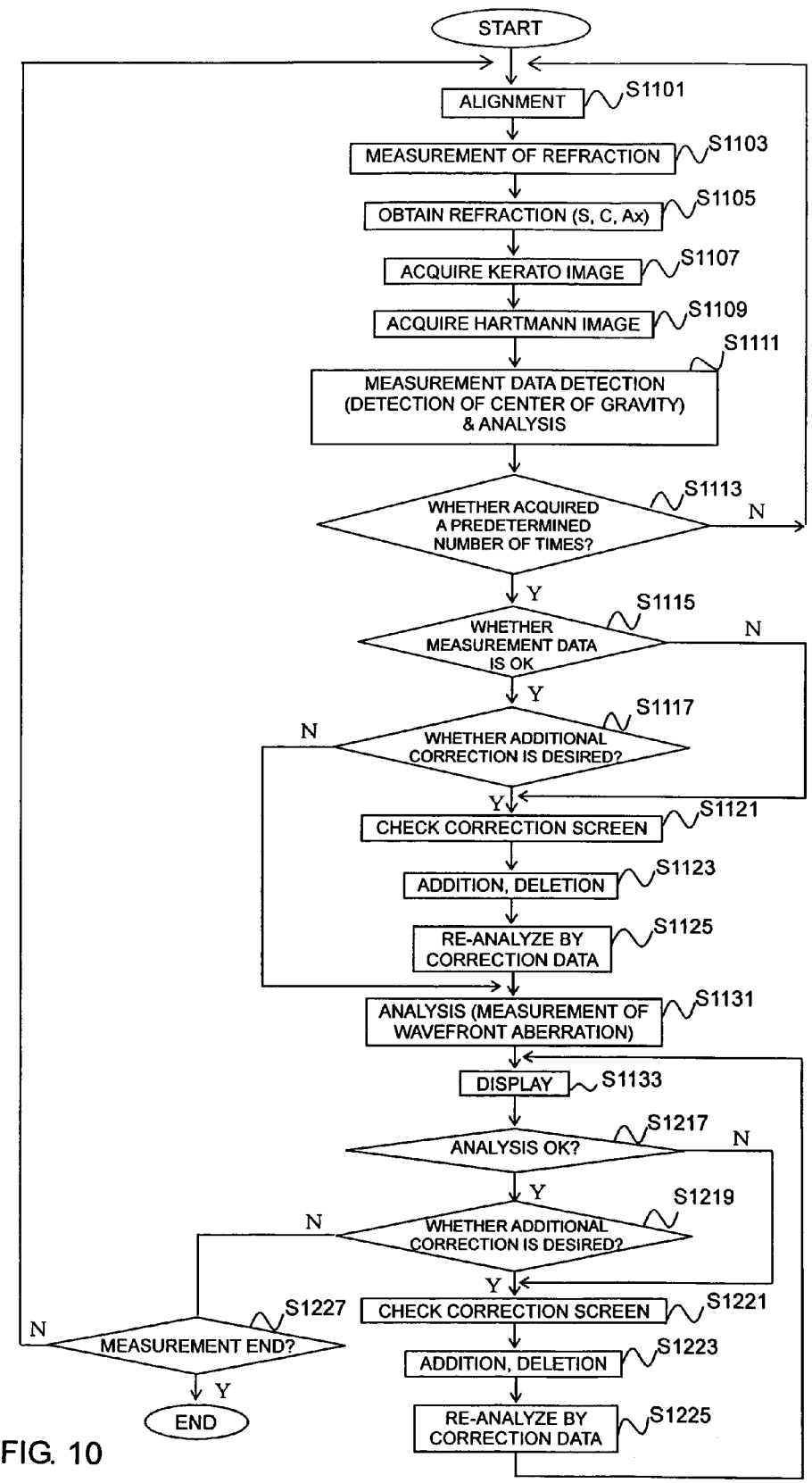
FIG. 10 is a flowchart of a third embodiment showing a specific measurement method of the eye characteristic measuring apparatus 1000.

FIG. 10 is a flowchart of a third embodiment showing a specific measurement method of the eye characteristic measuring apparatus 1000. Incidentally, processings overlapping with those of the flowcharts of the first and the second embodiments are denoted by the same symbols, and their functions are the same.

This flowchart is, for example, a combination of the flowchart of the first embodiment and the flowchart of the second embodiment. Specifically, in this flowchart, an analysis (measurement of eye optical characteristic such as wavefront aberration) is performed at step S1131 in the flowchart of the first embodiment, and after the display at step S1133 is performed, the processing of step S1217 to S1227 in the flowchart of the second embodiment is performed.

In this flowchart, before the analysis at step S1131, correction of data is performed by the first correction unit 603 in the confirmation correction mode, and further, also after the analysis at step S1131, the correction of data can be performed by the second correction unit 607 in the additional correction mode.

Incidentally, when the display of the check correction screen by the first correction unit 603 in the foregoing confirmation correction mode (S1121) and/or the display of the check correction screen by the second correction unit 607 in the additional correction mode (S1221) is performed, a mode for mass examination may be carried out. Specifically, data of plural test subjects and analysis (wavefront aberration) result obtained from the data are previously stored in the memory 800 as average (normal) data and analysis result, and at the time of mass examination, the measurement data judgment unit 601 and/or the measurement result judgment unit 605 compares data and analysis result of each individual subjected to the medical examination with the average (normal) data and analysis result, and may issue an alarm of re-measurement in the case where an inappropriate analysis result is obtained.

3. Eye Characteristic Measuring Apparatus (II)

Figure 11:
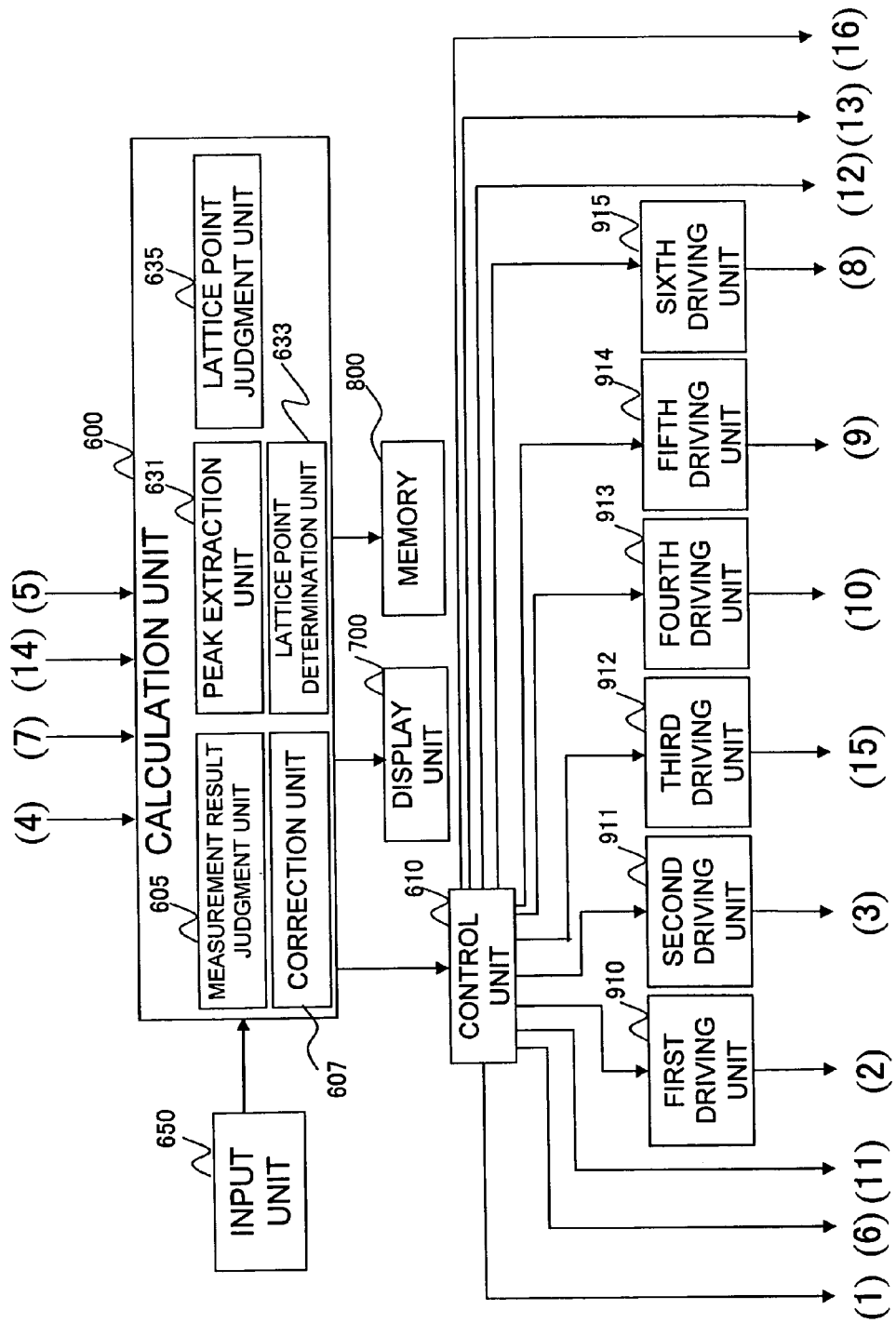
FIG. 11 is an electrical block diagram showing an electric structure of the eye characteristic measuring apparatus 1000 of the invention.

FIG. 11 is an electrical block diagram showing an electric structure of an eye characteristic measuring apparatus 1000 of the invention.

The electric driving system of the eye characteristic measuring apparatus 1000 includes a calculation unit 600, a control unit 610, an input unit 650, a display unit 700, a memory 800, a first driving unit 910, a second driving unit 911, a third driving unit 912, a fourth driving unit 913, a fifth driving unit 914, and a sixth driving unit 915. The calculation unit 600 includes, for example, a measurement result judgment unit 605, a correction unit 637, a peak extraction unit 631, a lattice point determination unit 633, a lattice point judgment unit 635, and a measurement unit for performing various eye characteristic measurements. Further, the input unit 650 includes a pointing device for indicating a suitable button displayed on the display unit 700, an icon, a position, an area and the like, a keyboard for inputting various data, and the like.

The calculation unit 600 is constructed such that the first signal (4) from the first light reception unit 510, the second signal (5) from the second light reception unit 520, the signal (7) from the third light reception unit 35, and the signal (14) from the light reception unit 54 are inputted. The calculation unit 600 obtains the optical characteristic of the subject eye 60 on the basis of the first signal (4) from the first light reception unit 510, and calculates a refractive power, a degree of astigmatism, and an astigmatic axis angle and detects the illumination state of the first illumination optical system 200A on the basis of the second signal (5) from the second light reception unit 520. Besides, the calculation unit 600 outputs signals corresponding to the calculation results to the control unit 610 for performing the whole control of the electric driving system, the display unit 700 (various display examples will be described later), and the memory 800. Incidentally, the calculation unit 600 obtains the optical characteristic of the subject eye 60 on the basis of the first signal from the first light reception unit 510 corresponding to the tilt angle of the light flux.

The peak extraction unit 631 performs, for example, peak extraction of a spot image on the basis of the first signal from the first light reception unit 510. The lattice point determination unit 633 determines lattice point coordinates by determining column numbers of lattice points from a vicinity of a center axis in the horizontal direction on the basis of the peaks of the spot images extracted by the peak extraction unit 631, and then by determining row numbers on the basis of positions of the spot images with the determined column numbers.

The lattice point judgment unit 635 judges, for example, whether the lattice point determined by the lattice point determination unit 633 is appropriate. In the case where the lattice point judgment unit 635 judges, for example, that the lattice point coordinate determined by the lattice point determination unit 633 is inappropriate, the lattice point determination unit 633 again determines the lattice point in an axial direction different from the direction of the previously determined axis (for example, the horizontal direction, the vertical direction).

The calculation unit 600 calculates the wavefront aberration of the subject eye 60 as the optical characteristic on the basis of the lattice point coordinates of the respective spots determined by the lattice point determination unit 633. The measurement result judgment unit 605 judges whether the wavefront aberration obtained by the calculation unit 600 is appropriate. When the measurement result judgment unit 605 judges that a measurement result is inappropriate, the correction unit 637 causes the check correction screen to be displayed and corrects it into appropriate measurement data.

The control unit 610, and the first to the sixth driving units 910 to 915 have the same structures and operations as those described in the section of "2. Eye Characteristic Measuring Apparatus (I)".

Flowchart of First Embodiment

Figure 12:
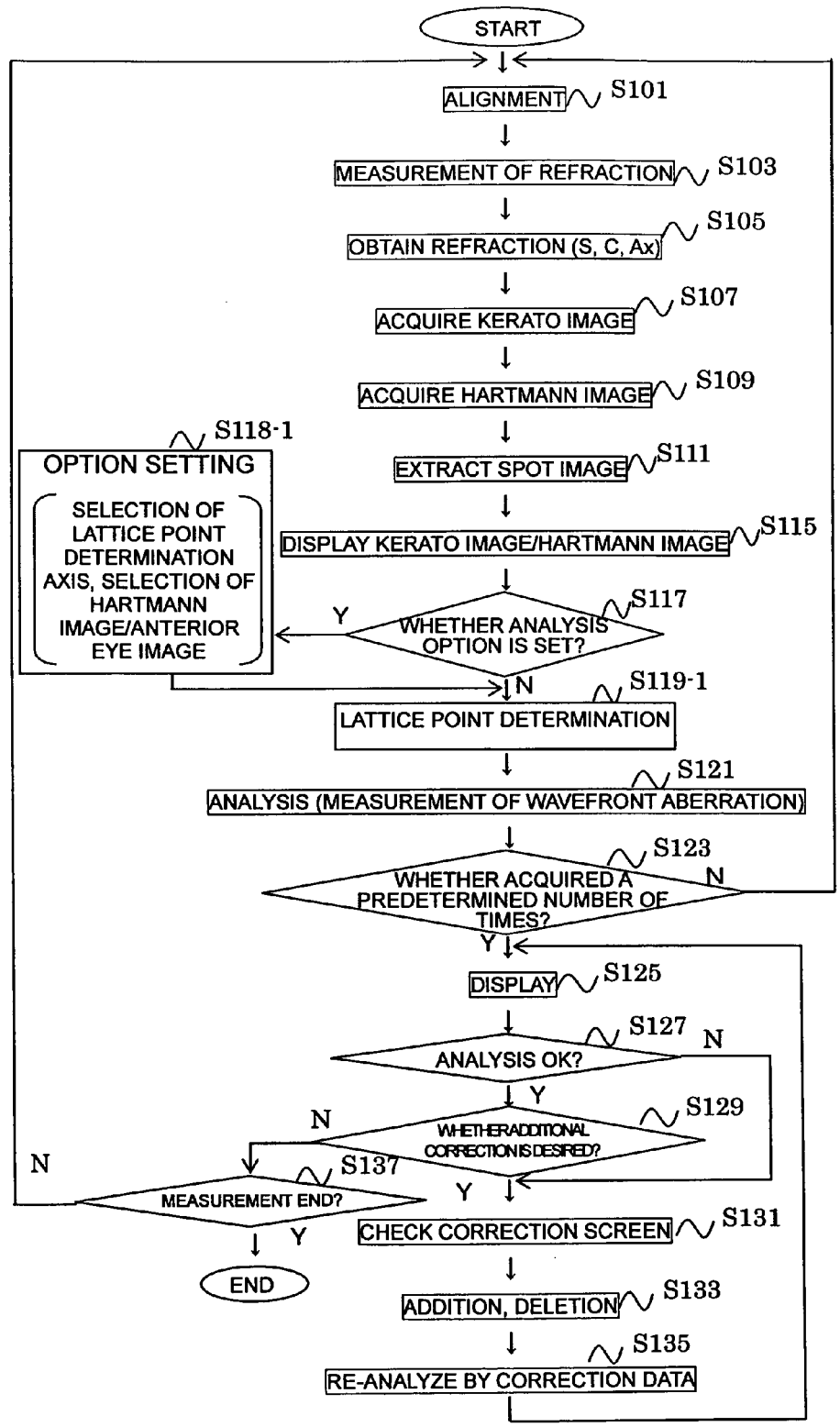
FIG. 12 is a flowchart of a first embodiment showing a specific measurement method of the eye characteristic measuring apparatus 1000.

FIG. 12 is a flowchart of a first embodiment showing a specific measurement method of the eye characteristic measuring apparatus 1000. The flowchart here shows such a processing that when spots of a Hartmann image are made to correspond to lattice point coordinates, after an automatic analysis mode for determining the lattice point coordinates from the horizontal direction is carried out, the calculation/display of the wavefront aberration is performed, and then, it is judged whether the analysis result has been appropriate, and in the case where the analysis result is inappropriate, the check correction screen is displayed or displayed by the instruction of the checker, and after correction, the wavefront aberration is calculated and the display is performed.

When the measurement is started, first, the alignment adjustment of the position of the subject eye 60 is performed (S101). Here, for example, in accordance with the instruction of the checker, the control unit 610 controls a specified driving unit on the basis of the control signal from the calculation unit 600, performs an alignment, and puts the subject eye 60 and the optical system of the eye characteristic measuring apparatus 1000 into an appropriate arrangement.

Next, after the alignment adjustment, the calculation unit 600 performs the measurement of refractions by an auto refract meter (S103). The calculation unit 600 obtains the refractions such as a refractive power, a degree of astigmatism, and an astigmatic-axis angle (S, C, Ax) on the basis of the measurement at step S103 (S105). After step S105, the calculation unit 600 acquires a kerato image by the third light reception unit 35 of the third light reception optical system 30 (S107). Incidentally, at step S107, although the kerato image is used, instead thereof, a Placido ring image may be acquired. Further, the calculation unit 600 acquires a Hartmann image by the first light reception unit 510 of the first light reception optical system 300A (S109).

The peak extraction unit 631 extracts spot images of the Hartmann image acquired at step S109 (S111). The calculation unit 600 displays the kerato image/Hartmann image (S115). Next, the lattice point determination unit 633 judges whether analysis option setting is to be performed (S117), and in the case where the analysis option setting is to be performed, the option setting (selection of the lattice point determination axis, selection of Hartmann image/anterior eye image, etc.) is performed (S118-1). On the other hand, in the case where the analysis option setting is not to be performed at step S117, or after the option setting of step S118-1, the lattice point determination part 633 again determines the lattice point (S119-1: automatic analysis mode). Incidentally, this option setting may be previously set before the measurement is started.

Hereinafter, the processing (step S119-1) of the automatic analysis mode ("Hartmann image" "anterior eye image") of the lattice point determination unit 633 will be described.

Figure 13:
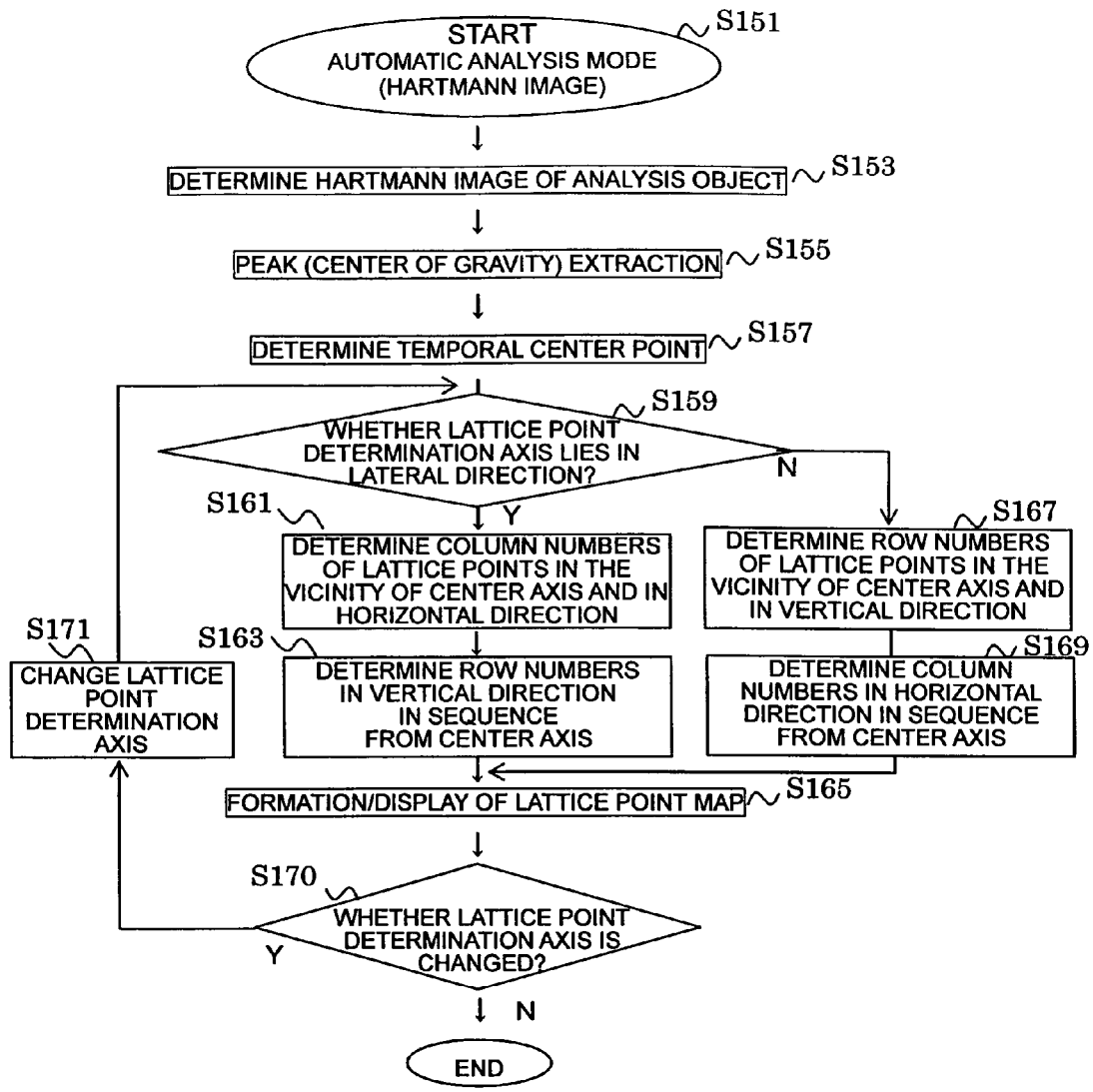
FIG. 13 is a flowchart (1) showing a processing of an automatic analysis mode (Hartmann image).

FIG. 13 is a flowchart (1) showing the processing of the automatic analysis mode (Hartmann image).

First, when the lattice point determination unit 633 proceeds to the automatic analysis mode (Hartmann image) (S151), the lattice point determination unit 633 determines the Hartmann image of the analysis object (S153). The peak extraction unit 631 performs peak (center of gravity) extraction of the spot image of the Hartmann image of the analysis object (S155). The lattice point determination unit 633 determines a temporal center point on the basis of the peak of the spot image extracted at step S155 (S157). Next, the lattice point determination unit 633 judges whether the lattice point determination axis selected at the option setting performed at step S118-1 lies in the lateral direction (S159).

For example, in the case where the lattice point determination axis lies in the lateral direction at step S159, the lattice point determination unit 633 determines the column numbers of the lattice points in the vicinity of the center axis and in the lateral direction (S161), and then, determines the row numbers in the vertical direction in sequence from the center axis (S163). Incidentally, the processing of step S161 and S163 is a first mode in which priority is given to the horizontal direction. On the other hand, in the case where the lattice point determination axis lies in the vertical direction at step S159, the lattice point determination unit 633 determines the row numbers of the lattice points in the vicinity of the center axis and in the vertical direction (S167), and then, determines the column numbers in the lateral direction in sequence from the center axis (S169). Incidentally, the processing of step S167 and S169 is a second mode in which priority is given to the vertical direction. Next, the lattice point determination unit 633 forms a lattice point map in which the row numbers and the column numbers are given to the lattice points, and displays it (S165). The selection of the first mode and the second mode can be performed by selecting "with option setting" at step S117 of "analysis option setting?", and by performing the processing of "selection of lattice point determination axis" by the input unit 650 at step S118-1. Here, for example, as a default value, the lattice point determination axis can be made to lie in the lateral direction.

Figure 14:
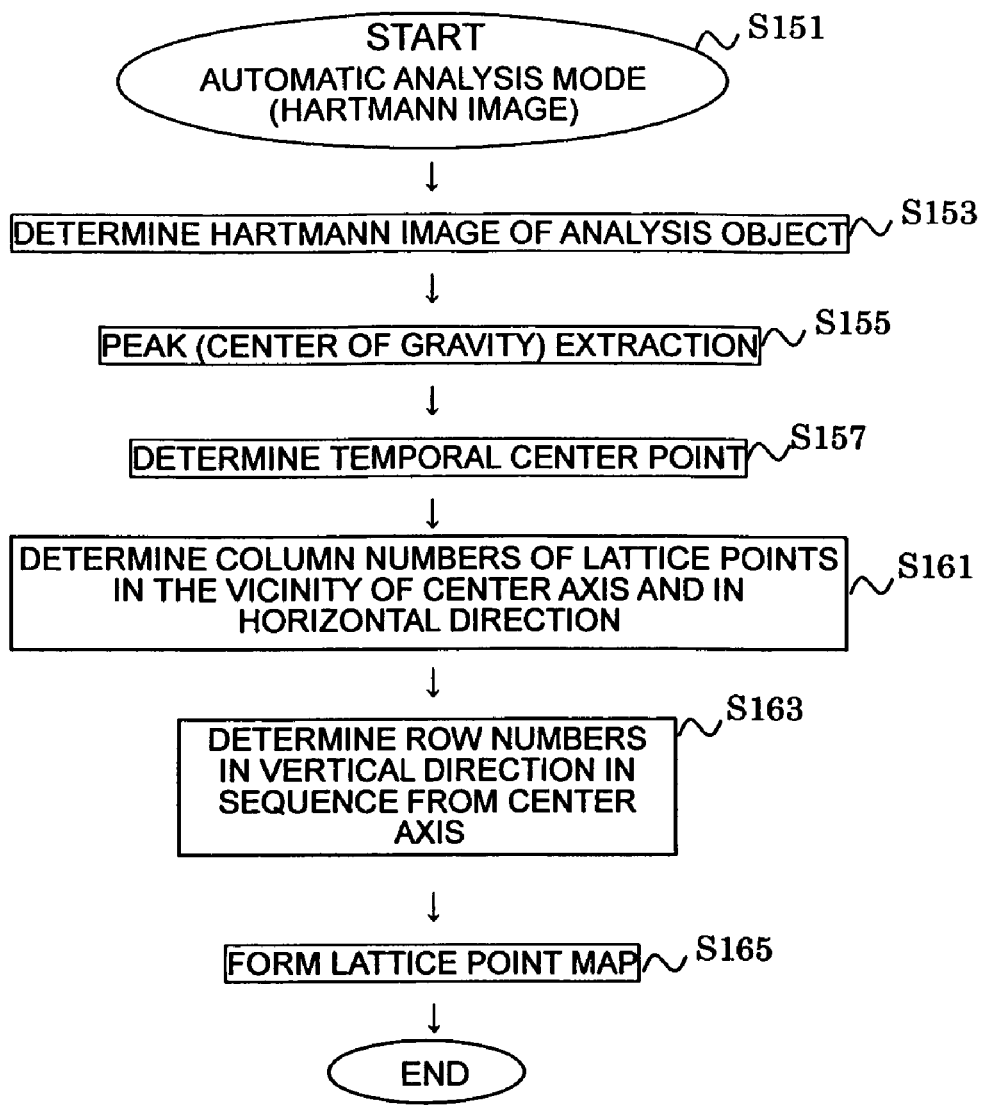
FIG. 14 is a flowchart showing a processing of an automatic analysis mode in a case of only lateral direction.

Besides, the steps S159, S167 and S169 are omitted, and the processing may be performed only by the first mode at the steps S161 and S163 in which priority is given to the lateral direction. FIG. 14 shows a flowchart expressing the processing of the automatic analysis mode in the case of only the lateral direction. The operation of each step is similar to the processing of the foregoing corresponding step.

FIG. 15 is a view showing spots when row and column numbers are given to lattice points.

The lattice point determination unit 633 determines column numbers of lattice points in the vicinity of the center axis and in the lateral direction at step S161. A description will be given to a case where the lattice point determination axis lies in the lateral direction. In the case where there occurs a shift from a reference lattice point, in the spot images of the Hartmann image, for example, there is a tendency that the lattice intervals in the horizontal direction are substantially constant, and the lattice intervals in the vertical direction become uneven (FIG. 15(*a*)). As the cause thereof, for example, as a tendency of astigmatism, since astigmatism with the rule often occurs in which the astigmatic axis angle is close to verticalness, it is supposed that the Hartmann image contracts in the vertical direction. FIG. 15(*a*) shows a determination example of the column numbers of the lattice points in the horizontal direction. First, the lattice point determination unit 633 makes an appropriate position the center (0, 0) when correspondence of lattice points is performed, and gives column numbers to the respective lattice points in the horizontal direction. Here, they are ((−5, 0), . . . , (0, 0), . . . , (5, 0)). After giving the column numbers to the respective lattice points in the lateral direction, the lattice point determination unit 633 determines the row numbers of the lattice points in the vertical direction in sequence from the center axis at step S163. The lattice point determination unit 633 determines the row numbers of the lattice points in the vicinity of the center and in the vertical direction at step S167.

Next, a description will be given to a case where the lattice point determination axis lies in the vertical direction. With respect to an eye with astigmatism against the rule, abnormal cornea, failure of a cornea operation or the like can be uneven in the lattice interval in the horizontal direction (FIG. 15(*b*)). FIG. 15(*b*) shows a determination example of row numbers of lattice points in the vertical direction. First, the lattice point determination unit 633 makes an appropriate position the center (0, 0) when correspondence of the lattice points is performed, and gives row numbers to the respective lattice points in the vertical direction. Here, they are ((0, −5), . . . , (0, 0), . . . , (0, 5)). After giving the row numbers to the respective lattice points in the vertical direction, the lattice point determination unit 633 determines, as described above, the column numbers of the lattice points in the lateral direction in sequence from the center axis at step S169.

At step S170, the lattice point map displayed at step S165 is confirmed, and in the case where it is judged to be appropriate to change the lattice point determination axis, for example, in the case where the intervals of the spot images in the selected lattice point determination axis direction are uneven, the procedure proceeds to step S171. Specifically, the measurement result judgment unit 605 can judge the propriety of the lattice point map by, for example, one of or a combination of following conditions on the basis of the obtained spot images.

Whether the whole density of spot images is a predetermined value or higher?

Whether the number of extracted spots is a predetermined number or higher?

Whether the level of spot images is a predetermined level or higher?

At step S171, the lattice point determination axis presently set is changed, that is, the axis is changed to the lateral direction in the case where it is set to the vertical direction, and on the contrary, the axis is changed to the vertical direction in the case where it is set to the lateral direction. The procedure proceeds to step S159, and a lattice point map is newly formed in accordance with the changed lattice point determination axis. In the case where it is judged to be unnecessary to change the lattice point determination axis at step S170, the automatic analysis mode is ended, and the procedure proceeds to step S121.

Here, a return is made to FIG. 12 again and a description will be made. The calculation unit 600 performs analysis (measurement of optical characteristic such as wavefront aberration) (S121), and judges whether the measurement data detected at step S121 is acquired at a predetermined number of times (S123). In the case where it is not acquired the predetermined number of times, a return is made to step S101 again, and the processing subsequent to the alignment adjustment is performed. On the other hand, in the case where the measurement data is acquired the predetermined number of times at step S123, the calculation unit 600 displays analysis results of various display objects at step S121 on the display unit 700 (S125). The display objects include, for example, a center of gravity/lattice map as an retinal image calculated at the foregoing processing, a keratoring or a Placido ring extracted as a cornea image, a pupil edge, a wavefront measurement value, an anterior eye image, a Hartmann image, a refraction, a wavefront aberration and the like. The measurement result judgment unit 605 judges whether the analysis result at step S121 is appropriate (S127).

The measurement result judgment unit 605 can judge the propriety of the analysis result by one of or a combination of following conditions, for example, at step S127.

Whether a component of a defocus term ($Z_2^0$, described later) of Zernike coefficients of wavefront components is close to zero?

Whether Zernike coefficients of an aberration of a cornea of large refractivity and those of a wavefront aberration of a subject eye have the same tendency?

Whether it is similar to the data of personal medical record (in a previously measured database) when they are compared with each other?

Whether plural newly measured data of the same subject eye are the same when they are compared with each other?

Next, in the case where the analysis result is inappropriate at step S127, the correction unit 637 automatically displays a check correction screen on the display unit 700 and proceeds to an additional correction mode (S131).

Here, the additional correction mode will be described. Incidentally, the coordinate values of lattice points attached in the "number" mode described later are the row and column numbers of the lattice points determined at step S119.

FIG. 4 is the view showing the display example of the check correction screen.

Next, cases where these mode selection buttons ("point", "net", "number") are respectively selected on the check correction screen in accordance with the instruction of the checker, will be specifically described.

FIG. 5 is the view showing check correction screens in the cases where the mode selection buttons are respectively selected.

Here, a return is made to FIG. 12 again and a description will be made. The correction unit 637 performs addition and deletion of spots on the check correction screen (S133). Hereinafter, step S133 will be described.

FIG. 6 is the view showing the case where the execution button "detection of center of gravity of spot" on the check correction screen is selected.

As the processing at step S133, for example, in the case where the execution button "detection of center of gravity of spot" is selected on the check correction screen, when an area to which addition of the center of gravity of a spot is desired is selected by the proper checker using the input unit 650 such as the pointing device or the keyboard, the correction unit 637 performs the detection of the center of gravity of the spot. In order to surround the area to which the addition of the center of gravity of the spot is desired, it is possible to mention such instances that for example, a mouse pointer is moved onto a diagonal line of a rectangle, an ellipse or the like, or it is surrounded by a free curved line.

Incidentally, in the detection of the center of gravity of the spot, in an area including all spots, the center of gravity can be detected by changing the threshold of the light quantity level at the time when the spot is extracted. For example, in the detection of the center of gravity of the spot, for example, an area containing the blur of the spot is surrounded by a rectangle or an ellipse, and the whole shading is also considered, for example, the background of shading and noise components are removed, so that the center of gravity of the spot can be detected (shading correction). Although the detection of the center of gravity is made at one point for each area in this case, it is also possible to make such a setting that detection is made at plural points in the area.

FIG. 7 is the view showing the case where the execution button "erasure of point" on the check correction screen is selected.

As the processing at step S133, for example, in the case where the execution button "erasure of point" is selected on the check correction screen, when the area where deletion of the center of gravity of the spot is desired by the proper checker using the input unit 650 such as the pointing device or the keyboard, the correction unit 637 detects it, and deletes the center of gravity of the spot in the area. Here, in order to delete the center of gravity of the spot, the area containing the center of gravity of the spot, the deletion of which is desired, can be surrounded in the same method as that of the case where the center of gravity of the spot is detected.

FIG. 8 is the view showing the case where the execution button "dummy point" on the check correction screen is selected.

First, FIG. 8(a) shows the state where the "point" mode is selected. Here, a spot is not extracted in the area A. Thus, the measurement result judgment unit 605 judges that the analysis result is inappropriate at step S127. FIG. 8(b) shows the state where the "net" mode is selected. Here, since the spot is not extracted in the area A of FIG. 8(a), the correspondence of the lattice in the vicinity of the area A is erroneous. FIG. 8(c) shows the state where the "number" mode is selected. Here, since the spot is not extracted in the area A of FIG. 8(a), the coordinate values of spots in the vicinity of the area A are given while the area A is skipped.

Here, in order to make the correspondence to the correct lattice points, as the processing at step S133, for example, in the case where the execution button "dummy point" is selected on the check correction screen, when a place (for example, a point contained in the area A) to which the addition of the dummy point, which is not used for aberration analysis, is desired is selected by the proper checker using the input unit 650 such as the pointing device or the keyboard, the correction unit 637 adds the dummy point to that place. When the dummy point is added into the area A, the respective spots become substantially uniform, and the check correction screen becomes, for example, the check correction screens of the respective modes shown in FIG. 5.

Here, a return is made to FIG. 12 again and a description will be made. After the "OK" button is pressed, the calculation unit 600 performs re-analysis on the basis of the correction data added/deleted at step S133 (S135).

Next, the calculation unit 600 displays the analysis result by the re-analysis at step S135 on the display unit 700 (S125). Even if the analysis result is appropriate at step S127, the calculation unit 600 judges whether the proper checker desires additional correction (S129). In the case where the checker desires the additional correction at step S129, the correction unit 637 performs the foregoing step S131. On the other hand, in the case where the additional correction is not desired, the calculation unit 600 judges whether the measurement is to be ended (S137), and in the case where the measurement is to be ended, the measurement is ended. On the other hand, in the case where the measurement is not to be ended at step S137, a return is made to step S101 again, and the processing subsequent to the alignment adjustment is performed.

Here, the option setting at step S118-1 will be further described. As described above, the lattice point determination unit 633 changes the lattice point determination axis (here, the lateral axis is changed to the vertical axis) in accordance with the instruction of the input unit 650 for providing instructions of the processing concerning the correction of the lattice point, and further, can set the following option. That is, although the automatic analysis mode is processed with respect to the Hartmann image in the above, it can be processed with respect to the anterior eye image (kerato image, Placido ring, or the like) ("selection of Hartmann image, anterior eye part line"). When this mode is set, instead of step S119-1 described in detail in FIG. 13, a following flowchart is executed. In this flowchart, instead of the lattice point, a ring number obtained from the Placido ring image is determined.

Figure 16:
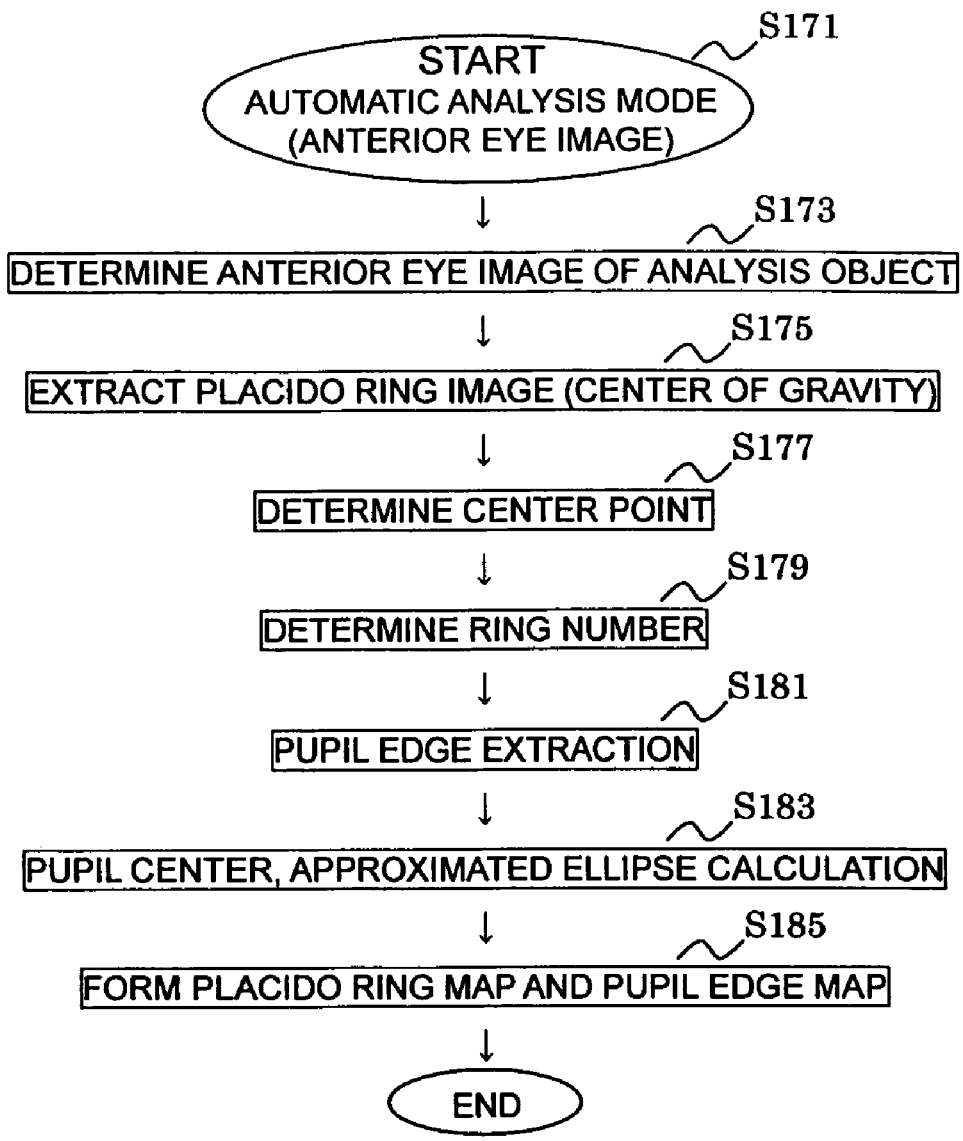
FIG. 16 is a flowchart showing a processing of an automatic analysis mode (anterior eye image).

FIG. 16 is a flowchart showing the processing of the automatic analysis mode (anterior eye image).

First, when the lattice point determination unit 633 proceeds to the automatic analysis mode (anterior eye image) (S171), the lattice point determination unit 633 determines, for example, the anterior eye image of the analysis object (S173). The peak extraction unit 631 performs (the center of gravity) extraction of the Placido ring image of the anterior eye image of the analysis object (S175). The lattice point determination unit 633 determines the center point on the basis of the center of gravity of the Placido ring image extracted at step S175 (S177).

Next, the lattice point determination unit 633 determines the ring number of the Placido ring image on the basis of the center point determined at step S177 (S179). The lattice point determination unit 633 extracts the pupil edge (S181), and calculates the pupil center, and approximated ellipse (S183). Further, the lattice point determination unit 633 forms the keratoring map or Placido ring map, and the pupil edge map (S185).

Figure 17:
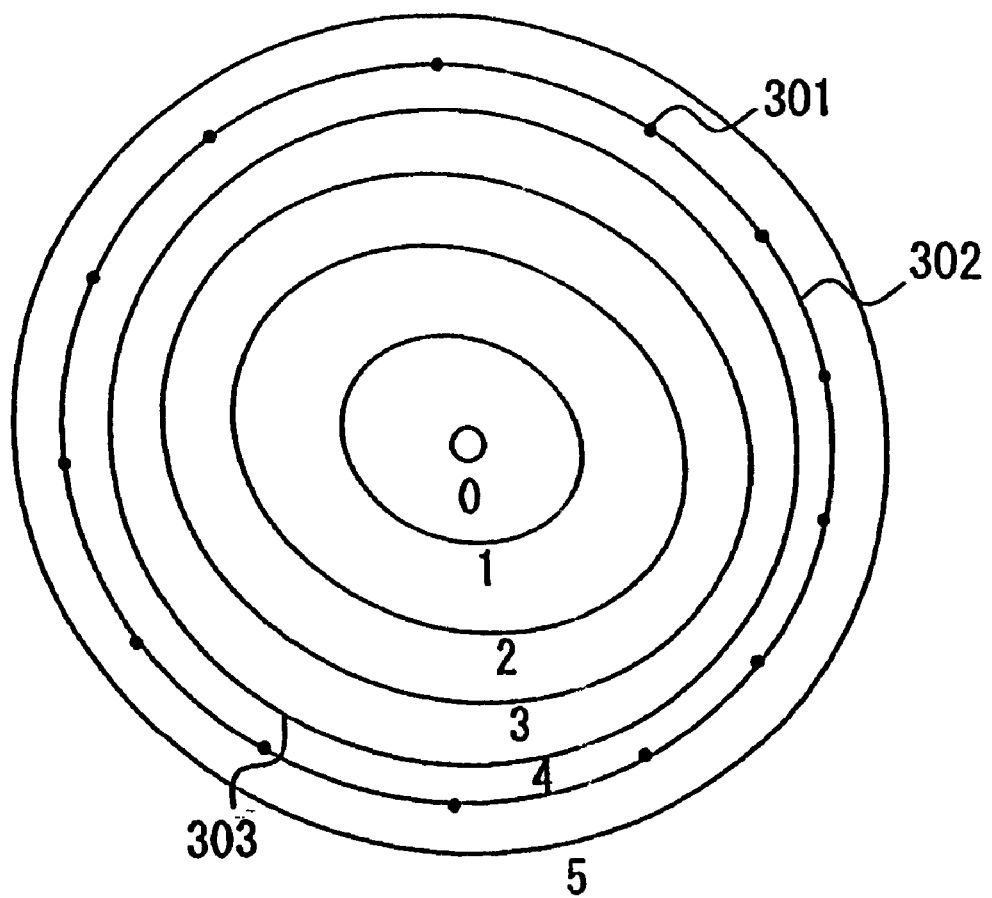
FIG. 17 is an explanatory view of a Placido ring map and a pupil edge map.

FIG. 17 is an explanatory view of a Placido ring map and a pupil edge map.

Here, as the pupil edge map, for example, a pupil edge 302 including plural pupil edge points 301 is shown, and further, as the Placido ring map, for example, plural rings 303 are shown. Incidentally, ring numbers (here, 0, 1, 2, 3, 4 and 5) are given to the respective rings 303.

When the processing concerning the anterior eye image is set, instead of the processing of steps S131 to S133, a following correction (addition, deletion, etc.) processing is carried out as the need arises. For example, in the case where the pupil edge point extracted at step S181 is corrected, the lattice point determination unit 633 performs addition/deletion of the pupil edge point in accordance with the instruction of the input unit 650. In the case where the point of the center of gravity of the Placido ring extracted at step S175 is corrected, the lattice point determination unit 633 performs the addition/deletion of the point of the center of gravity of the Placido ring. In the case where the ring number determined at step S179 is changed, the lattice point determination unit 633 changes the ring number.

Flowchart of Second Embodiment

Figure 18:
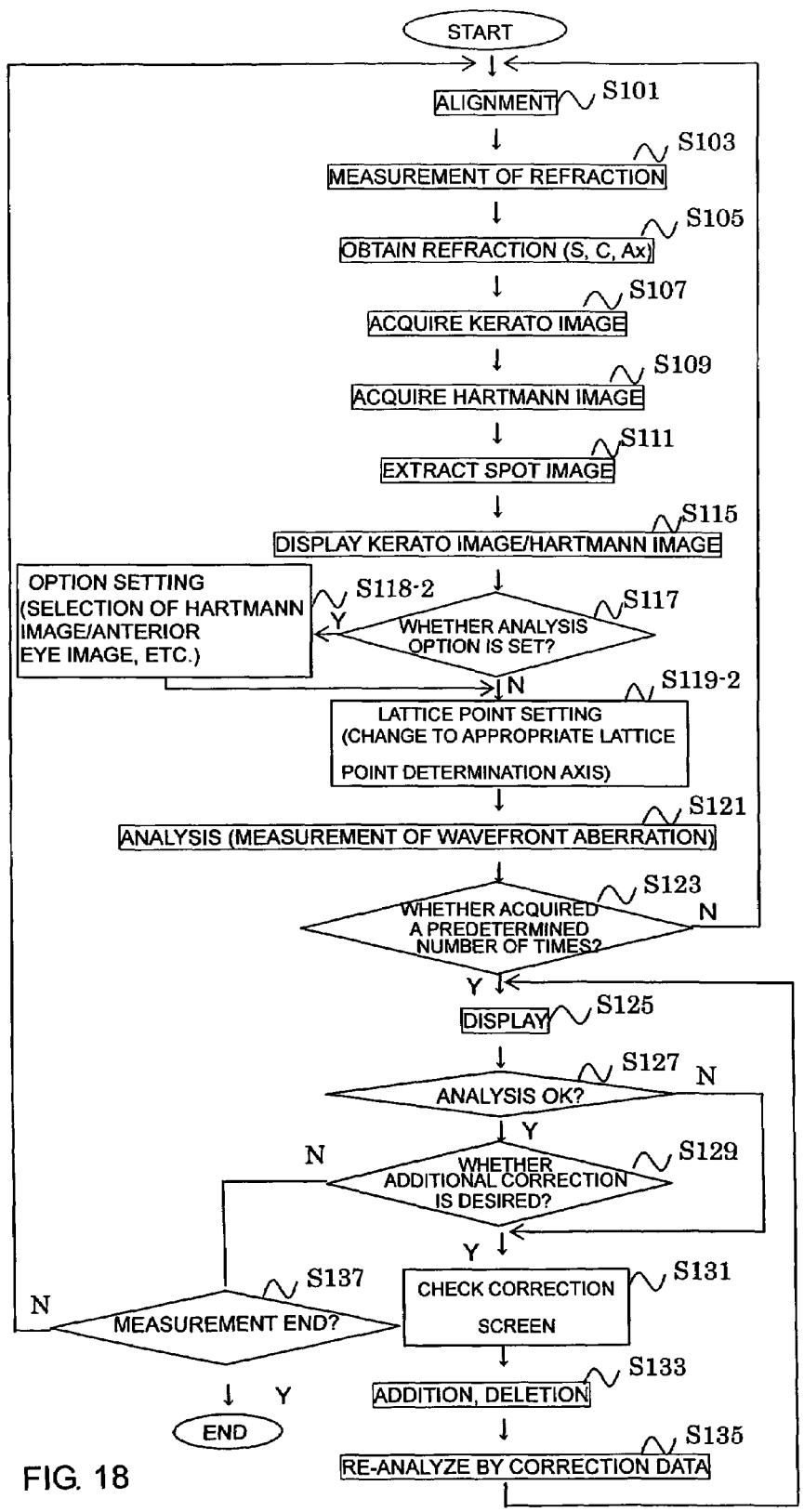
FIG. 18 is a flowchart of a second embodiment showing a specific measurement method of the eye characteristic measuring apparatus 1000.

FIG. 18 is a flowchart of a second embodiment showing a specific measurement method of the eye characteristic measuring apparatus 1000. Incidentally, processings overlapping with those of the flowchart of the first embodiment are denoted by the same symbols, and their functions are the same.

The flowchart here indicates a processing in which when spots of a Hartmann image and lattice points are made to correspond to each other, a direction in which lattice points are determined can be changed (for example, the horizontal direction is changed to the vertical direction). The other processings overlap with those of the foregoing flowchart.

In this flowchart, instead of the processing (step S118-1, S119-1) included in the automatic analysis mode in the flowchart of the first embodiment, the processing of step S118-2 and S119-2 is performed. At step S118-2, the selection of the lattice point determination axis is not performed, and the selection of the Hartmann image or the anterior eye image can be performed. Hereinafter, especially the processing of the automatic analysis mode ("Hartmann image") of the lattice point determination unit 633 will be described. Incidentally, in the case where the automatic analysis mode (anterior eye image) is selected, the processing is the same as that in the description of the first embodiment, for example, the flowchart (S171 to S185) of FIG. 16 and their description.

The processing of the automatic analysis mode (step S119-2) will be described in brief. First, with respect to the display of the kerato image/Hartmann image at step S115, the lattice point judgment unit 635 judges, for example, whether the lattice point is properly extracted. Next, in the case where lattice points are not properly extracted, after changing the order of the lattice point determination axis, the lattice point determination unit 633 again determines lattice points. On the other hand, in the case where the lattice points are properly extracted, the lattice point determination unit 633 determines the lattice points.

Figure 19:
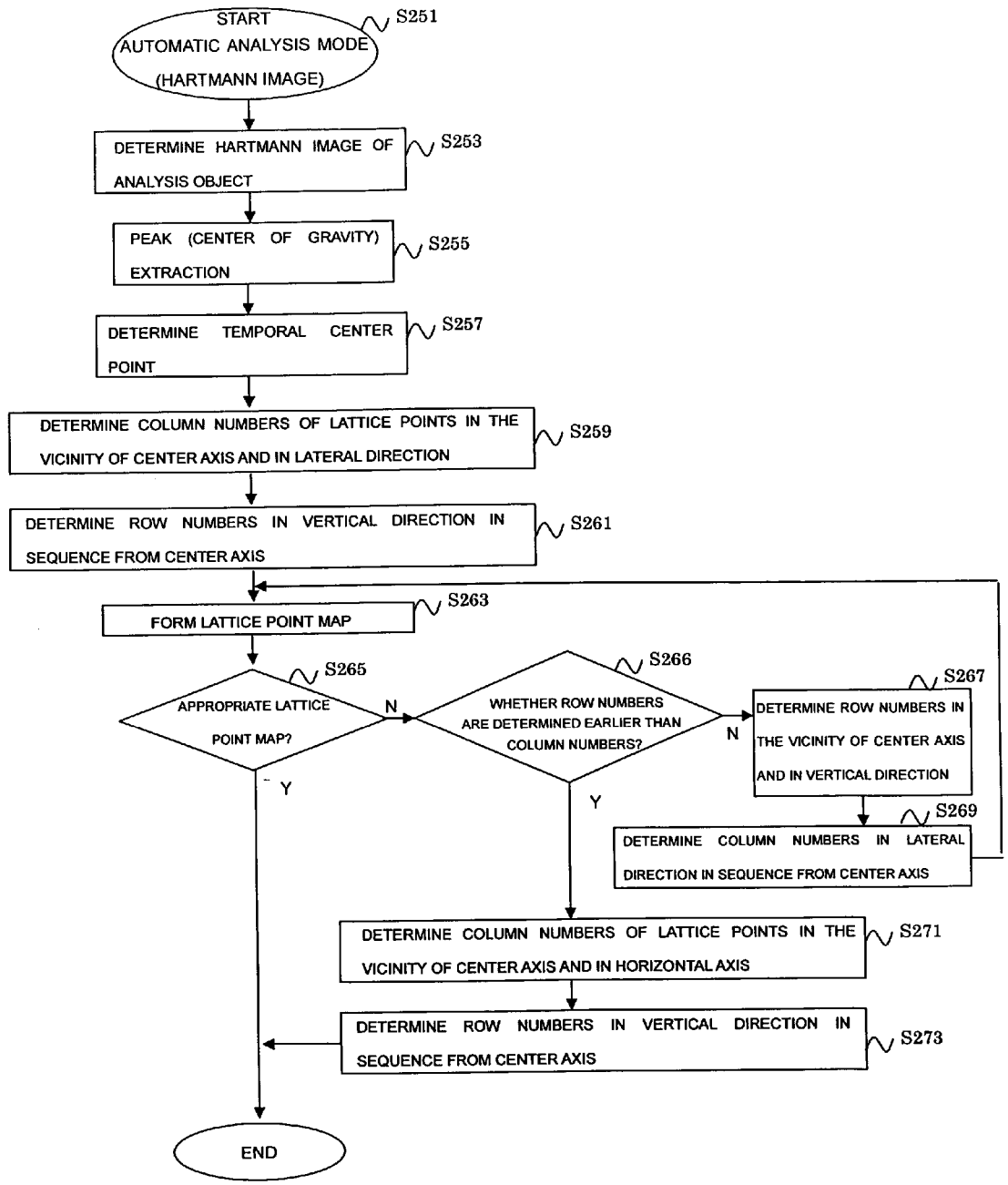
FIG. 19 is a flowchart (2) showing a processing of an automatic analysis mode (Hartmann image).

FIG. 19 is a flowchart (2) showing the processing of the automatic analysis mode (Hartmann image).

First, when the lattice point analysis unit 633 proceeds to the automatic analysis mode (Hartmann image) (S251), the lattice point determination unit 633 determines the Hartmann image of the analysis object (S253). The peak extraction unit 631 extracts the peak (the center of gravity) of the determined Hartmann image (S255). Next, the lattice point determination unit 633 determines a temporal center point (S257), determines column numbers of lattice points in the vicinity of the center axis and in the horizontal direction (S259), and then, the row numbers are determined in the vertical direction in sequence from the center axis (S261). Incidentally, the processing of step S259 and S261 has the first mode in which priority is given to the horizontal direction.

Next, the lattice point determination unit 633 forms the lattice point map on the basis of the determined row and column numbers of the lattice points (S263). Here, the lattice point judgment unit 635 judges whether the lattice point map formed at step S263 is appropriate (S265). The lattice point judgment unit 635 can judge the propriety of the lattice point map at step S265 by one of or a combination of following conditions.

Whether the whole density of spot images is a predetermined value or higher?

Whether the number of extracted spots is a predetermined number or higher?

Whether the level of spot images is a predetermined level or higher?

When the lattice point map is appropriate, the lattice point determination unit 633 ends the automatic analysis mode. On the other hand, in the case where the lattice point map formed at step S265 is inappropriate, the lattice point determination unit 633 judges whether row numbers in the vertical direction are determined earlier than column numbers of the lattice points in the lateral direction (S266). If the row numbers in the vertical direction have not been determined, the row numbers in the vicinity of the center axis and in the vertical direction are determined (S267), and then, the row numbers are determined in the lateral direction in sequence from the center axis (S269). Further, the lattice point determination unit 633 forms again the lattice point map on the basis of the determined row and column numbers of the lattice points. Incidentally, the processing of step S267 and S269 is the second mode in which priority is given to the vertical direction. If the row numbers have already been determined before, the column numbers are again determined (S271), and next, the row numbers are determined in the vertical direction (S273). If data in which the column numbers were again first determined remains in the memory, the process of S271 and S273 is omitted, and the data of the lattice points which is determined from the column numbers remaining in the memory can also be used. In the case where priority is given to the case where the row numbers are given in the vertical direction, the process of S271 and S273 can also be omitted. Then, the automatic analysis mode is ended.

In this flowchart, after a lattice point map is formed in the first mode, in the case where the lattice point map is inappropriate, a lattice point map is automatically formed in the second mode. Incidentally, after the second mode, the first mode is executed and the lattice point map may be formed.

When the display (S125) of the check correction screen by the correction unit 637 in the foregoing additional correction mode is performed, the mode for mass examination may be carried out. Specifically, data of plural test subjects and the analysis (wavefront aberration) result obtained from this data are previously stored in the memory 800 as the average (normal) data and analysis result, and further, at the mass examination, the measurement result judgment unit 605 compares data and analysis result of each individual subjected to the medical examination with the average (normal) data and analysis result, and in the case where an inappropriate analysis result is obtained, an alarm for re-measurement may be issued.

INDUSTRIAL APPLICABILITY

According to the invention, as described above, irrespective of the state of a subject eye, the wavefront aberration of the subject eye can be more efficiently and properly measured and can be displayed. Besides, according to the invention, before measurement and/or after measurement of the wavefront aberration, a correction operation is performed in an efficient procedure, and the measurement of the wavefront aberration can be again performed.

Besides, according to the invention, spot images of a Hartmann image and lattice point coordinates are made to correspond to each other, and an illumination state can be made appropriate.

The invention claimed is:

1. An eye characteristic measuring apparatus comprising:
    a light source unit for emitting a light flux with a first wavelength;
    a first illumination optical system for illuminating a small area on a retina of a subject eye with the light flux from the light source unit;
    a first light reception optical system for leading a part of a first reflected light flux reflected by and returning from the retina of the subject eye to be received through a first conversion member for converting it into at least substantially 17 beams;
    a first light reception unit for receiving the received light flux of the first light reception optical system to form a first signal;
    a measurement data judgment unit for judging, on the basis of the first signal from the first light reception unit, whether measurement data is appropriate for obtaining a wavefront aberration;
    a first correction unit for causing a check correction screen to be displayed when the measurement data judgment unit judges that the measurement data is inappropriate and for correcting it into appropriate measurement data;
    a calculation unit for calculating the wavefront aberration of the subject eye as optical characteristic on the basis of the measurement data which has been judged to be appropriate by the measurement data judgment unit or the measurement data which has been corrected by the first correction unit; and
    a display unit for displaying the wavefront aberration as a calculation result of the calculation unit.

2. An eye characteristic measuring apparatus according to claim 1, wherein the measurement data judgment unit judges propriety of the measurement data on the basis of density of spot images of a Hartmann image and/or the number of extracted spot images.

3. An eye characteristic measuring apparatus according to claim 1, further comprising an input unit for providing an instruction of a display mode,
    wherein the display unit displays the measurement data in one of or a combination of more than one of a first mode in which centers of gravity of spots acquired from the first light reception unit are displayed, a second mode of displaying a state in which the spots are connected to each other in a lattice form, and a third mode of displaying a state in which coordinate values are given to the respective spots.

4. An eye characteristic measuring apparatus according to claim 1, further comprising an input unit for providing an instruction of a processing concerning correction of a spot,
    wherein in an area on the check correction screen, the first or the second correction unit detects the center of gravity of a spot in the area in accordance with the instruction of the input unit, and adds the center of gravity of the spot for use in calculation by the calculation unit.

5. An eye characteristic measuring apparatus according to claim 1, further comprising an input unit for providing an instruction of a processing concerning correction of a spot,
    wherein the first or the second correction unit deletes the center of gravity of a spot on the check correction screen in accordance with the instruction of the input unit, and prevents the center of gravity of the deleted spot from being used for calculation of the wavefront aberration of the subject eye.

6. An eye characteristic measuring apparatus according to claim 1, further comprising an input unit for providing an instruction of a processing concerning correction of a spot,
    wherein the first or the second correction unit adds, for use in calculation by the calculation unit, a dummy point, which becomes the center of gravity of a spot, onto the check correction screen in accordance with the instruction of the input unit.

7. An eye characteristic measuring apparatus comprising:
    a light source unit for omitting a light flux with a first wavelength;
    a first illumination optical system for illuminating a small area on a retina of a subject eye with the light flux from the light source unit;
    a first light reception optical system for leading a part of a first reflected light flux reflected by and returning from the retina of the subject eye to be received through a first conversion member for converting it into at least substantially 17 beams;
    a first light reception unit for receiving the received light flux of the first light reception optical system to form a first signal;
    a calculation unit for calculating a wavefront aberration of the subject eye as optical characteristic on the basis of the measurement data of the first signal from the first light reception unit;
    a measurement result judgment unit for judging whether the wavefront aberration obtained by the calculation part is appropriate;
    a second correction unit for causing a check correction screen to be displayed when the measurement result judgment unit judges that a measurement result is inappropriate and for correcting it into appropriate measurement data; and
    a display unit for displaying the wavefront aberration as a calculation result of the calculation unit.

8. An eye characteristic measuring apparatus according to claim 7, wherein the measurement result judgment unit judges propriety of the measurement result on the basis of one of or a combination of more than one of conditions of whether a component of a defocus term of wavefront components is close to zero, whether Zernike coefficients of a cornea and a wavefront have a same tendency, whether measurement data in a database in which measurement data of the subject eye is previously stored and newly measured measurement data are substantially identical to each other when they are compared with each other, and whether plural measurement data measured for the same subject eye are substantially identical to each other when they are compared with each other.

9. An eye characteristic measuring apparatus comprising:
    a light source unit for emitting a light flux with a first wavelength;
    a first illumination optical system for illuminating a small area on a retina of a subject eye with the light flux from the light source unit;
    a first light reception optical system for leading a part of a first reflected light flux reflected by and returning from the retina of the subject eye to be received through a first conversion member for converting it into at least substantially 17 beams;
    a first light reception unit for receiving the received light flux of the first light reception optical system to form a first signal;
    a measurement data judgment unit for judging, on the basis of the first signal from the first light reception unit, whether measurement data is appropriate for obtaining a wavefront aberration;
    a first correction unit for causing a check correction screen to be displayed when the measurement data judgment unit judges that the measurement data is inappropriate and for correcting it into appropriate measurement data;
    a calculation unit for calculating the wavefront aberration of the subject eye as optical characteristic on the basis of the measurement data which has been judged to be appropriate by the measurement data judgment unit or the measurement data which has been corrected by the first correction unit;
    measurement result judgment unit for judging whether the wavefront aberration obtained by the calculation part is appropriate;
    a second correction unit for causing the check correction screen to be displayed when the measurement result data judgment unit judges that a measurement result is inappropriate and for correcting it into appropriate measurement data; and
    a display unit for displaying the wavefront aberration as a calculation result of the calculation unit.

10. An eye characteristic measuring apparatus according to claim 9, wherein the measurement data judgment unit judges propriety of the measurement data on the basis of density of spot images of a Hartmann image and/or the number of extracted spot images, and
    the measurement result judgment unit judges propriety of the measurement result on the basis of one of or a combination of more than one of conditions of whether a component of a defocus term of wavefront components is close to zero, whether Zernike coefficients of a cornea and a wavefront have a same tendency, whether measurement data in a database in which measurement data of the subject eye is previously stored and newly measured measurement data are substantially identical to each other when they are compared with each other, and whether plural measurement data measured for the same subject eye are substantially identical to each other when they are compared with each other.

11. An eye characteristic measuring apparatus comprising:
    a light source unit for emitting a light flux with a first wavelength;

a first illumination optical system for illuminating a small area on a retina of a subject eye with the light flux from the light source unit;

a first light reception optical system for leading a part of a first reflected light flux reflected by and returning from the retina of the subject eye to be received through a first conversion member for converting it into at least substantially 17 beams;

a first light reception unit for receiving the received light flux of the first light reception optical system to form a first signal;

a peak extraction unit for extracting a peak of a spot image on the basis of the first signal from the first light reception unit;

a lattice point determination unit for determining a lattice point in a first mode in which a column number of a lattice point is determined from a vicinity of a center axis in a horizontal direction on the basis of the peak of the spot image extracted by the peak extraction unit, and then a row number is determined on the basis of a position of the spot image of the determined column number;

a calculation unit for calculating a wavefront aberration of the subject eye as optical characteristic on the basis of the lattice point determined by the lattice point determination unit; and a display unit for displaying the wavefront aberration as a calculation result of the calculation unit.

12. An eye characteristic measuring apparatus according to claim 11, further comprising an input unit for providing an instruction of a mode for determining a lattice point, wherein the lattice point determination unit determines the lattice point in a second mode in which a row number of a lattice point is determined from a vicinity of a center axis in a vertical direction on the basis of the peak of the spot image extracted by the peak extraction unit, and then a column number is determined on the basis of a position of the spot image of the determined row number.

13. An eye characteristic measuring apparatus according to claim 11, characterized in that the display unit displays the spot image extracted by the peak extraction unit or a lattice point map.

14. An eye characteristic measuring apparatus according to claim 11 further comprising:

a measurement result judgment unit for judging whether the wavefront aberration obtained by the calculation unit is appropriate; and a correction unit for causing a check correction screen to be displayed when the measurement result judgment unit judges that a measurement result is inappropriate and for correcting it into appropriate measurement data.

15. An eye characteristic measuring apparatus according to claim 14, wherein the measurement result judgment unit judges propriety of the measurement result on the basis of one of or a combination of more than one of conditions of whether a component of a defocus term of wavefront components is close to zero, whether Zernike coefficients of a cornea and a wavefront have a same tendency, whether measurement data in a database in which measurement data of the subject eye is previously stored and newly measured measurement data are substantially identical to each other when they are compared with each other, and whether plural measurement data measured for the same subject eye are substantially identical to each other when they are compared with each other.

16. An eye characteristic measuring apparatus according to claim 14, further comprising an input unit for providing an instruction of a processing concerning correction of a spot, wherein the correction unit adds, for use in calculation by the calculation unit, a lattice point having not been extracted by the peak extraction unit as a dummy point, which becomes the center of gravity of the spot, onto the check correction screen in accordance with the instruction of the input unit.

17. An eye characteristic measuring apparatus comprising:

a light source unit for emitting a light flux with a first wavelength;

a first illumination optical system for illuminating a small area on a retina of a subject eye with the light flux from the light source unit;

a first light reception optical system for leading a part of a first reflected light flux reflected by and returning from the retina of the subject eye to be received through a first conversion member for converting it into at least substantially 17 beams;

a first light reception unit for receiving the received light flux of the first light reception optical system to form a first signal;

a peak extraction unit for extracting a peak of a spot image on the basis of the first signal from the first light reception unit;

a lattice point determination unit for determining one of a row number and a column number of a lattice point from a vicinity of an axis on the basis of the peak of the spot image extracted by the peak extraction unit, and then determining the other of the column number and the row number from the determined one of the numbers on the basis of a position of the spot image;

a calculation unit for calculating a wavefront aberration of the subject eye as optical characteristic on the basis of the lattice point determined by the lattice point determination unit; and a display unit for displaying the wavefront aberration as a calculation result of the calculation unit.

18. An eye characteristic measuring apparatus according to claim 17, wherein the lattice point determination unit determines the column number of the lattice point from the vicinity of the axis in a horizontal direction on the basis of the peak of the spot image extracted by the peak extraction unit, and then, determines the row number on the basis of the position of the spot image of the determined column number.

19. An eye characteristic measuring apparatus according to claim 17, further comprising a lattice point judgment unit for judging whether a lattice point coordinate determined by the lattice point determination unit is appropriate, wherein in a case where the lattice point judgment unit judges that the lattice point coordinate determined by the lattice point determination unit is inappropriate, the lattice point determination unit again determines a lattice point in an axial direction different from a previously determined axial direction.

20. An eye characteristic measuring apparatus according to claim 19, wherein the lattice point judgment unit judges propriety of measurement data on the basis of density of spot images of a Hartmann image and/or the number of the extracted spot images.

* * * * *